United States Patent
Scott et al.

(10) Patent No.: US 6,458,387 B1
(45) Date of Patent: Oct. 1, 2002

(54) SUSTAINED RELEASE MICROSPHERES

(75) Inventors: Terrence L. Scott, Winchester; Larry R. Brown, Newton; Frank J. Riske, Stoughton; Charles D. Blizzard, Westwood; Julia Rashba-Step, Newton, all of MA (US)

(73) Assignee: Epic Therapeutics, Inc., Norwood, MA (US)

(*) Notice: Subject to any disclaimer, the term of this patent is extended or adjusted under 35 U.S.C. 154(b) by 0 days.

(21) Appl. No.: 09/420,361

(22) Filed: Oct. 18, 1999

(51) Int. Cl.$^7$ .............. A61K 9/14; A61K 9/16; A61K 9/50

(52) U.S. Cl. ............... 424/489; 424/490; 424/484; 424/488; 424/499

(58) Field of Search ............... 424/484, 488, 424/489, 499, 490

(56) References Cited

U.S. PATENT DOCUMENTS

| | | | |
|---|---|---|---|
| 4,612,008 A | * 9/1986 | Wong et al. | |
| 4,744,933 A | 5/1988 | Rha et al. | 264/4.3 |
| 4,925,677 A | 5/1990 | Feijen | 424/484 |
| 5,008,116 A | 4/1991 | Cahn | 424/491 |
| 5,160,745 A | 11/1992 | Deluca et al. | 424/487 |
| 5,595,760 A | 1/1997 | Cherif-Cheikh | 424/464 |
| 5,637,309 A | 6/1997 | Tajima et al. | 424/423 |
| 5,981,719 A | * 11/1999 | Woiszwillo et al. | |

FOREIGN PATENT DOCUMENTS

| | | |
|---|---|---|
| EP | 0 351 296 A | 1/1990 |
| EP | 0 357 401 | 3/1990 |
| EP | 1 060 741 A1 A1 | 12/2000 |
| JP | 08 225454 | 9/1996 |
| WO | WO 99/48479 A | 9/1999 |

OTHER PUBLICATIONS

US 5,849,884, 12/1998, Woiszwillo et al. (withdrawn)
Remingtons Pharmaceutical Sciences, eighteenth edition, 1990, p 1306.*

* cited by examiner

Primary Examiner—Gollamudi S. Kishore
Assistant Examiner—Amy E Pulliam
(74) Attorney, Agent, or Firm—Wolf, Greenfield & Sacks P.C.

(57) ABSTRACT

Methods for forming sustained release microspheres and the products produced thereby are provided. The microspheres have a smooth surface that includes a plurality of channel openings that are less than 1000 angstroms in diameter.

28 Claims, 7 Drawing Sheets

SUSTAINED RELEASE MICROSPHERES

FIELD OF THE INVENTION

This invention relates to methods and compositions for forming and using sustained release microspheres. The microspheres are porous and include a plurality of channel openings that are less than 1000 angstroms in diameter.

BACKGROUND OF THE INVENTION

Microparticles, microspheres, and microcapsules, referred to herein collectively as "microparticles", are solid or semi-solid particles having a diameter of less than one millimeter, more preferably less than 100 microns, which can be formed of a variety of materials, including synthetic polymers, proteins, and polysaccharides. Microparticles have been used in many different applications, primarily separations, diagnostics, and drug delivery.

The most well known examples of microparticles used in separations techniques are those which are formed of polymers of either synthetic or protein origin, such as polyacrylamide, hydroxyapatite or agarose. These polymeric microparticles are commonly used to separate molecules such as proteins based on molecular weight and/or ionic charge or by interaction with molecules chemically coupled to the microparticles.

In the diagnostic area, microparticles are frequently used to immobilize an enzyme, substrate for an enzyme, or labeled antibody, which is then interacted with a molecule to be detected, either directly or indirectly.

In the controlled drug delivery area, molecules are encapsulated within microparticles or incorporated into a monolithic matrix, for subsequent release. A number of different techniques are routinely used to make these microparticles from synthetic polymers, natural polymers, proteins and polysaccharides, including phase separation, solvent evaporation, emulsification, and spray drying. Generally the polymers form the supporting structure of these microspheres, and the drug of interest is incorporated into the polymer structure. Exemplary polymers used for the formation of microspheres include homopolymers and copolymers of lactic acid and glycolic acid (PLGA) as described in U.S. Pat. No. 5,213,812 to Ruiz, U.S. Pat. No. 5,417,986 to Reid et al., U.S. Pat. No. 4,530,840 to Tice et al., U.S. Pat. No. 4,897,268 to Tice et al., U.S. Pat. No. 5,075,109 to Tice et al., U.S. Pat. No. 5,102,872 to Singh et al., U.S. Pat. No. 5,384,133 to Boyes et al., U.S. Pat. No. 5,360,610 to Tice et al., and European Patent Application Publication Number 248,531 to Southern Research Institute; block copolymers such as tetronic 908 and poloxamer 407 as described in U.S. Pat. No. 4,904,479 to Illum; and polyphosphazenes as described in U.S. Pat. No. 5,149,543 to Cohen et al. Microspheres produced using polymers such as these exhibit a poor loading efficiency and are often only able to incorporate a small percentage of the drug of interest into the polymer structure. Therefore, substantial quantities of microspheres often must be administered to achieve a therapeutic effect.

Spherical beads or particles have been commercially available as a tool for biochemists for many years. For example, antibodies conjugated to beads create relatively large particles specific for particular ligands. The large antibody-coated particles are routinely used to crosslink receptors on the surface of a cell for cellular activation, are bound to a solid phase for immunoaffinity purification, and may be used to deliver a therapeutic agent that is slowly released over time, using tissue or tumor-specific antibodies conjugated to the particles to target the agent to the desired site.

The most common method of covalently binding an antibody to a solid phase matrix is to derivative a bead with a chemical conjugation agent and then bind the antibody to the activated bead. The use of a synthetic polymeric bead rather than a protein molecule allows the use of much harsher derivatization conditions than many proteins can sustain, is relatively inexpensive, and often yields a linkage that is stable to a wide range of denaturing conditions. A number of derivatized beads are commercially available, all with various constituents and sizes. Beads formed from synthetic polymers such as polyacrylamide, polyacrylate, polystyrene, or latex are commercially available from numerous sources such as Bio-Rad Laboratories (Richmond, Calif.) and LKB Produkter (Stockholm, Sweden). Beads formed from natural macromolecules and particles such as agarose, crosslinked agarose, globulin, deoxyribose nucleic acid, and liposomes are commercially available from sources such as Bio-Rad Laboratories, Pharmacia (Piscataway, N.J.), and IBF (France). Beads formed from copolymers of polyacrylamide and agarose are commercially available from sources such as IBF and Pharmacia. Magnetic beads are commercially available from sources such as Dynal Inc. (Great Neck, N.Y.).

One disadvantage of the microparticles or beads currently available is that they are difficult and expensive to produce. Microparticles produced by these known methods have a wide particle size distribution, often lack uniformity, and fail to exhibit long term release kinetics when the concentration of active ingredients is high. Furthermore, the polymers used in these known methods are dissolved in organic solvents in order to form microspheres. The microspheres must therefore be produced in special facilities designed to handle organic solvents. These organic solvents could denature proteins or peptides contained in the microparticles. Residual organic solvents could be toxic when administered to humans or animals.

In addition, the available microparticles are rarely of a size sufficiently small to fit through the aperture of the size of needle commonly used to administer therapeutics or to be useful for administration by inhalation. For example, microparticles prepared using polylactic glycolic acid (PLGA) are large and have a tendency to aggregate. A size selection step, resulting in product loss, is necessary to remove particles too large for injection. PLGA particles that are of a suitable size for injection must be administered through a large gauge needle to accommodate the large particle size, often causing discomfort for the patient.

Generally all currently available microspheres are activated to release their contents in aqueous media and therefore must be lyophilized to prevent premature release. In addition, particles such as those prepared using the PLGA system exhibit release kinetics based on both erosion and diffusion. In this type of system, an initial burst or rapid release of drug is observed. This burst effect can result in unwanted side effects in patients to whom the particles have been administered.

Microparticles prepared using lipids to encapsulate target drugs are currently available. For example, lipids arranged in bilayer membranes surrounding multiple aqueous compartments to form particles may be used to encapsulate water soluble drugs for subsequent delivery as described in U.S. Pat. No. 5,422,120 to Sinil Kim. These particles are generally greater than 10 $\mu$m in size and are designed for intra articular, intrathecal, subcutaneous and epidural administration. Alternatively, liposomes have been used for intravenous delivery of small molecules. Liposomes are spherical particles composed of a single or multiple phospholipid and cholesterol bilayers. Liposomes are 30 μm or greater in size and may carry a variety of water-soluble or lipid-soluble drugs. Liposome technology has been hindered by problems including purity of lipid components, possible toxicity, vesicle heterogeneity and stability, excessive uptake and manufacturing or shelf-life difficulties.

Therefore, there is an on-going need for development of new methods for making microparticles, particularly those that can be adapted for use in the separations, diagnostic and drug delivery area. Preferably, such improved microparticles would permit the sustained release of active agents in a predictable, consistent manner.

SUMMARY OF THE INVENTION

The invention solves these and other problems by providing methods and compositions for the sustained release of therapeutic and/or diagnostic agents in vivo and in vitro. As subsequently used herein the term "therapeutic agent" is intended to be inclusive of clinical agents which can be administered in microcapsular form, whether used primarily for treatment or diagnosis.

According to one aspect of the invention, a microsphere having a smooth surface which includes a plurality of channel openings is provided. The channel openings have a diameter which is less than 1000 angstroms as determined by gas adsorption technique for pore sizing. The microspheres of the invention include a macromolecule, preferably a protein or a nucleic acid, and at least one water soluble polymer. In general, the microspheres are formed by contacting the macromolecule and at least one water soluble polymer under aqueous conditions to form the microspheres, and the microspheres are then stabilized by either chemical crosslinking or exposing the microspheres to an energy source, preferably heat, or both, at a temperature which results in microspheres which are resistant to physical and chemical treatments such as sonication and caustic solutions under these conditions. Although not wishing to be bound to any particular theory or mechanism, it is believed that the microspheres form during the mixing step; however, such initially formed microspheres are transient and require a further step (e.g., including a crosslinking agent in the mixture and/or by applying heat or other energy source) to stabilize the transiently-formed microspheres. The particular conditions for forming representative microspheres of the invention are described in the Examples. In the preferred embodiments, the formation reaction is conducted in the absence of the addition of oils or organic solvents. Oil is defined as a substance that is liquid fat which is insoluble in water.

The protein component of the microsphere may be a carrier protein or a therapeutic protein (see, e.g., Table 1). As used herein, a "carrier protein" refers to a protein which has a molecular weight of at least about 1500 and which exists as a three dimensional structure. The carrier protein can also be a therapeutic protein, i.e., a protein which has a therapeutic activity; however, in general, the phrase "carrier protein" will be used in this application to refer to a protein which has a primary function to provide a three dimensional structure for the purpose of microsphere formation, even if the carrier protein also may have a secondary function as a therapeutic agent. In certain preferred embodiments, the carrier protein is an albumin, particularly, human serum albumin. The protein microspheres of the invention, optionally, further include a therapeutic agent such as a steroid (e.g., estradiol, testosterone, prednisolone, dexamethasone, hydrocortisone, lidocaine base, procaine base), or any other such chemical entity known to bind to the protein, preferably albumin, such as GCSF, or paclitaxel. In yet other embodiments (discussed below), the microspheres of the invention further include a complexing agent and, more preferably, a therapeutic agent (preferably a peptide) which is associated with the complexing agent via an ionic or nonionic interaction. In certain other embodiments, the protein that comprises the matrix is a therapeutic protein (e.g., a hormone such as insulin or human growth hormone) and the microsphere is constructed and arranged to provide sustained release of the therapeutic protein in vivo. More preferably, the microsphere is constructed and arranged to provide sustained release of the therapeutic agent in the absence of significant swelling of the microsphere.

Surprisingly, the surface of the microsphere is different from the interior. Extensive water washing of freeze fractured microspheres dissolves much of the microsphere matrix material leaving a thin shell. In addition, the surface of the microsphere is smooth; the channel (pore) openings are less than 1000 angstroms in diameter as determined by gas adsorption technique for por sizing using, e.g., BET technology for data analysis.

In general, the microspheres of the invention are formed by mixing the macromolecule, preferably a protein or a nucleic acid, together with at least one water polymer under conditions which permit the water soluble polymer to remove water from ("dehydrate") the macromolecule within specified or preferred ratios of macromolecule to water soluble polymer. As used herein, a "water soluble polymer" of the invention refers to a polymer or mixture of polymers which is capable of removing water from or dehydrating the macromolecule or otherwise capable of causing volume exclusion. Thus, the preferred process involves volume exclusion using an entirely aqueous system with no oil or organic solvents involved.

Suitable water soluble polymers include soluble linear or branched polymers, preferably those having a high molecular weight. Polymers can be highly water soluble, moderately-water soluble, or slightly water soluble (greater than 2% wt/vol water soluble). The preferred water soluble polymers are water soluble or soluble in a water miscible solvent. The water soluble polymers may be solubilized by first being dissolved in a water miscible solvent and then combining the polymer solution with an aqueous solvent. In the particularly preferred embodiments, the water soluble polymers of the invention are selected from the water soluble polymers identified in Table 2. In certain embodiments, the microspheres of the invention are formed of proteins and water soluble polymers and contain from 40 to less than 100 (wt %) protein. The final microsphere product which has been stabilized using a crosslinking agent and/or exposure to an energy source such as heat does not swell significantly in the presence of water (i.e., it is not a hydrogel). In the particularly preferred embodiments, the water soluble polymer is a carbohydrate-based polymer. Thus, in certain preferred embodiments, the microsphere comprises: (1) a protein, preferably albumin; and (2) a carbohydrate-based water soluble polymer, preferably hetastarch, wherein the protein represents at least 40% and less than 100% by weight of the microsphere. Preferably, the carbohydrate-based polymer represents greater than 0% and less than or equal to 30% by weight of the microsphere. In these and other embodiments, the microspheres preferably further comprise an active agent, preferably a luteinizing hormone releasing hormone or analog thereof. In general, the microspheres of the invention, when contacted with a solution of active agent, are capable of incorporating at least 60%, more preferably at least 70%, at least 80%, or at least 90%, and most preferably, at least 95% or at least 98% of the active agent. The active agent-containing microspheres optionally are further stabilized by contacting the microspheres with the same types of crosslinking agents and using the same types of conditions described herein for initially stabilizing the microspheres.

According to another aspect of the invention, a microsphere further including a complexing agent is provided. The microsphere of this aspect includes: (1) a macromolecule such as a protein (e.g., albumin, as described above); (2) at least one water soluble polymer (e.g., hetastarch (hydroxyethylstarch), PEG/PVP); and (3) a complexing agent. As used herein, a complexing agent refers to a molecule which is capable of interacting with a therapeutic agent (discussed below) to facilitate loading, retaining and/or otherwise delaying the release of the therapeutic agent from the microsphere (see, e.g., Table 3). As with all aspects of the invention, these microspheres have a smooth surface which includes a plurality of channel openings that are less than 1000 angstroms in diameter as determined by gas adsorption technique for pore sizing and, preferably, do not contain detectable oil or organic solvent.

According to a particularly preferred aspect of the invention, a microsphere further including at least two complexing agents is provided. The microsphere of this aspect includes: (1) a macromolecule such as a carrier protein (e.g., albumin, as described above); (2) at least one water soluble polymer (e.g., hetastarch (hydroxyethylstarch), PEG/PVP); (3) a first complexing agent that is an anionic polysaccharide; and (4) a second complexing agent that is a divalent metal cation selected from the group consisting of calcium, magnesium, zinc, strontium, barium, manganese, and iron. A particularly preferred embodiment of this aspect of the invention is illustrated in Example 17. Calcium and magnesium are the preferred divalent metal cations.

As used herein, a complexing agent refers to a molecule which is capable of interacting with a therapeutic agent (discussed below) to facilitate loading, retaining and/or otherwise delaying the release of the therapeutic agent from the microsphere (see, e.g., Table 3). As with other aspects of the invention, these microspheres preferably have a smooth surface which includes a plurality of channel openings that are less than 1000 angstroms in diameter as determined by gas adsorption technique for pore sizing and, more preferably, do not contain detectable oil or organic solvent.

A preferred method of incorporating the complexing agent(s) is to combine the complexing agent(s) with a water soluble polymer in aqueous solution, then add the macromolecule, and stabilize the microspheres with heat and/or crosslinking agents.

In general, the complexing agent is an ionic complexing agent (i.e., the complexing agent is capable of an ionic interaction with a therapeutic agent (discussed below)) or a non-ionic complexing agent (i.e., the complexing agent is capable of a non-ionic (e.g., hydrophobic, mixed ionic/nonionic) interaction with a therapeutic agent or with another complexing agent). Exemplary complexing agents are provided in Table 3. Ionic complexing agents of the invention are further categorized into anionic complexing agents (i.e., complexing agents having a negative charge such as anionic polysaccharides, e.g., dextran sulfate, galacturonic acids, alginates, mannuronic acid, guluronic acid, hyaluronic acid, chondroitin sulfates, heparin, chitin, chitosan, glycosaminoglycans, proteoglycans) and cationic complexing agents (i.e., complexing agents having a positive charge). The preferred complexing agents of the invention are anionic polysaccharides and divalent metal cations selected from the group consisting of calcium and magnesium.

In certain embodiments, the complexing agent is an anionic complexing agent having the structure of formula I:

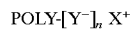
POLY-[Y$^-$]$_n$ X$^+$  I.

wherein POLY represents a principal chain of the anionic complexing agent which may be linear or branched;

wherein Y$^-$ represents an anionic group, e.g., sulfates, carboxyls, phosphates, nitrates, carbonates and the like, that may be coupled to any one or more of the branches of the principal chain;

wherein X$^+$ represents a cationic group, e.g., that is a counter ion to the anionic group;

wherein n is an integer from 1 to 10,000, preferably, from 5 to 100 and, more preferably, from 5 to 1000, and still more preferably, from 5 to 10,000; and wherein when n is greater than 1, the n Y$^-$ groups can be the same or different.

In yet other embodiments of the invention the complexing agent is a cationic complexing agent having the structure of formula II:

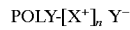
POLY-[X$^+$]$_n$ Y$^-$  II.

wherein POLY represents a principal chain of the cationic complexing agent which may be linear or branched;

wherein X$^+$ represents a cationic group, e.g., an amino group, that may be coupled to any one or more of the branches of the principal chain;

wherein Y$^-$ represents an anionic group, that is a counter ion to the cationic group;

wherein n is an integer from 1 to 10000, preferably, from 5 to 100 and, more preferably, from 5 to 1000, and most preferably, from 5 to 10,000; and wherein when n is greater than 1, the n X$^-$ groups can be the same or different.

According to another aspect of the invention, a microsphere further including an active agent is provided (see, e.g., Table 4). The microspheres into which the active agent can be loaded may include a complexing agent(s) to facilitate loading and/or modify the release of the active agent from the microsphere. Alternatively, the active agent can be loaded into the above-described microspheres which lack a complexing agent, e.g., the protein and/or the water soluble polymers of the invention can interact with the active agent to facilitate loading and/or modify its release from the microsphere. In general, although the active agent can be loaded into a microsphere of the invention during preparation of the microsphere, it is preferable to load the active agent into a preformed microsphere of the invention and, more preferable, to load the active agent into a preformed microsphere which contains a complexing agent(s) to facilitate loading and/or sustained release of the agent. In contrast to hydrogel microspheres, the microspheres of the invention do not swell significantly in water and, further, the microspheres do not require swelling in order to provide sustained release of the therapeutic protein and/or physiologically active agent from the microsphere.

As used herein, an active agent refers to an agent which has a diagnostic or therapeutic activity. Accordingly, an active agent can include a detectable label (e.g., a radioactive label) that is useful for identifying the locations of the released agent in vivo; Active agents also include therapeutic agents which are useful for treating a disease or condition. In certain embodiments, the preferred physiologically active agents are protein or peptide agents. Such protein or peptide agents typically can be further divided into categories, based upon the activity of the agent or the type of disease or condition that is being treated. The categories of physiologically active agents which can be used in the present invention include, but are not limited to, antibiotics, hematopoietics, antiinfective agents, antidementia agents, antiviral agents, antitumoral agents, antipyretics, analgesics, antiinflammatory agents, antiulcer agents, antiallergic agents, antidepressants, psychotropic agents, cardiotonics, antiarrythmic agents, vasodilators, antihypertensive agents such as hypotensive diuretics, antidiabetic agents, anticoagulants, cholesterol lowering agents, therapeutic agents for osteoporosis, hormones, vaccines and so on (see, e.g., Table 4).

The physiologically active peptide or protein which is employed in accordance with the present invention is a peptide composed of two or more amino acids. Preferably, such a peptide has a molecular weight greater than 200, e.g., in the range of about 200 to 200000. The more preferred molecular weight range is about 200 to 100000. More specific examples of physiologically active agents, including non-protein agents, which can be used in connection with the methods and compositions of the invention are provided in the detailed description of the invention.

According to still another aspect of the invention, a method for forming a microsphere is provided. The method involves: (1) forming an aqueous mixture containing a macromolecule, preferably a protein or a nucleic acid, and a water soluble polymer, preferably a carbohydrate-based polymer such as hetastarch; (2) allowing the microspheres to form in the aqueous mixture; (3) stabilizing the microspheres, preferably by contacting the microspheres with a crosslinking agent and/or exposing the microspheres to an energy source, preferably heat, under conditions sufficient to stabilize the microspheres; wherein the macromolecule is present in the aqueous mixture in an amount sufficient to form a microsphere that contains at least 40% and less than 100% by weight macromolecule. Although not wishing to be bound to any particular theory or mechanism, it is believed that the microspheres form during the mixing step; however, such initially formed microspheres are transient and require a further step (e.g., including a crosslinking agent in the mixture and/or by applying heat or other energy source) to stabilize the transiently-formed microspheres. Exemplary methods of preparing the microspheres are provided in the Examples.

According to yet another aspect of the invention, a pharmaceutical composition of matter and method of making said composition are provided. In certain embodiments, the composition includes a container containing a single dose of microspheres containing an active agent for treating a condition that is treatable by the sustained release of an active agent from the microspheres. The number of microspheres in the single dose is dependent upon the amount of active agent present in each microsphere and the period of time over which sustained release is desired. Preferably, the single dose is selected to achieve the sustained release of the active agent over a period of from about 1 to about 180 days, wherein the single dose of microspheres is selected to achieve the desired release profile for treating the condition.

According to another aspect of the invention, a syringe containing any of the microspheres disclosed herein is provided. For example, the composition can includes a syringe containing a single dose of microspheres containing an active agent for treating a condition that is treatable by the sustained release of the active agent from the microspheres. Preferably, a needle is attached to the syringe, wherein the needle has a bore size that is from 14 to 30 gauge.

Remarkably, the microspheres of the invention can be prepared to have a dimension which permits the delivery of microspheres using a needleless syringe (MediJector, Derata Corporation, Minneapolis, Minn. 55427), thereby eliminating the disposal problems inherent to needles which must be disposed as biohazard waste product. Thus, according to a particularly preferred aspect of the invention, a needleless syringe containing one or more doses of microspheres containing an active agent for treating a condition is provided. The microspheres can be prepared to have qualities suitable to be delivered by other parenteral and non-parenteral routes such as oral, buccal, intrathecal, nasal, pulmonary, transdermal, transmucosal and the like.

According to still other embodiments of the invention, nucleic acid-containing microspheres are provided. The nucleic acid-containing microspheres include: (1) a nucleic acid (e.g., plasmid, viral vector, oligonucleotide, RNA, antisense and missense nucleic acids); (2) a polycationic polymer (e.g., polylysine); and (3) a water soluble polymer (as described above). Thus, a method for forming the nucleic acid-containing microspheres is provided. The method involves: (1) combining, in one or more aqueous solutions, a nucleic acid, a polycationic polymer and a water soluble polymer to form an aqueous mixture which can be a mono- or multi-phase; and (2) subjecting the aqueous mixture to a crosslinking agent and/or an energy source under conditions (e.g., of concentration, incubation time) sufficient to stabilize a microsphere. Exemplary methods of forming the nucleic acid microspheres are provided in the Examples.

These and other aspects of the invention will be described in greater detail below. Throughout this disclosure, all technical and scientific terms have the same meaning as commonly understood by one of ordinary skill in the art to which this invention pertains unless defined otherwise.

DETAILED DESCRIPTION

The invention provides methods and compositions for the sustained release of therapeutic and/or diagnostic agents in vivo and/or in vitro. The microspheres have a generally uniform size and shape, ranging in size from about 0.5 microns to about 20 microns, depending upon the fabrication conditions. The characteristics of the microspheres may be altered during preparation by manipulating the water soluble polymer concentration, reaction temperature, pH, protein concentration, crosslinking agent, and/or the length of time the macromolecule is exposed to the crosslinking agent and/or the energy source.

The microspheres are useful for a wide variety of separations, diagnostic, therapeutic, industrial, commercial, cosmetic, and research purposes or for any purpose requiring the incorporation of and stabilization of an active molecule, reactant or drug. Thus, the microspheres of the invention are useful for medical and diagnostic applications, such as drug delivery, vaccination, gene therapy and histopathological or in vivo tissue or tumor imaging. Accordingly, the microspheres are suitable for oral or parenteral administration; mucosal administration; ophthalmic administration; intravenous, subcutaneous, intra articular, or intramuscular injection; administration by inhalation; and topical administration.

According to one aspect of the invention, a microsphere having a smooth surface which includes a plurality of channel openings is provided. Each channel opening has a diameter which is less than 1000 angstroms as determined by gas adsorption technique for pore sizing using, e.g., BET methodology for data analysis.

The microspheres are prepared by mixing or dissolving macromolecules with a water soluble polymer or mixture of water soluble polymers, such as linear or branched polymers of Table 2, at a pH near the isoelectric point of the macromolecule. The macromolecule and polymer mixture is exposed to a crosslinking agent and/or an energy source, such as heat, under conditions sufficient to stabilize the microspheres. The microspheres are then separated from the unincorporated reagents by separation methods such as filtration or centrifugation.

In general, the macromolecule or combination of macromolecules compose at least 40% and less than 100% by weight of the final weight of each microsphere. Preferably, the polymer concentration in the microsphere is greater than 0% and less than or equal to 30% by weight. The types of macromolecules forming the microspheres include, but are not limited to, proteins, peptides, carbohydrates, nucleic acids, viruses, or mixtures thereof.

Figure 13:
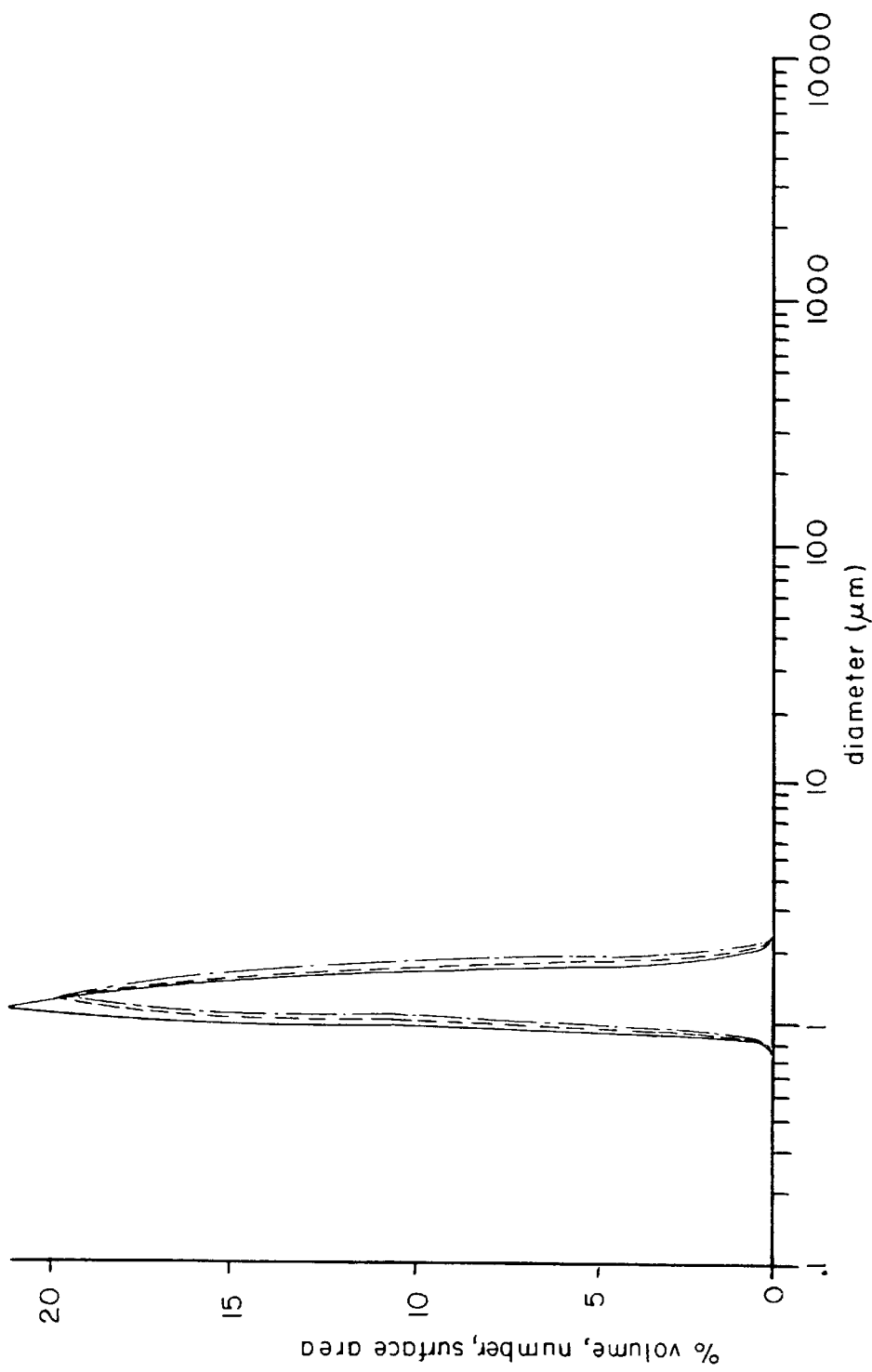
FIG. 13 shows a representative size distribution profile for the microspheres of the invention.

Each microsphere is composed of macromolecules and polymer molecules, which are intertwined or interspersed in the microsphere and are generally homogeneously distributed. Although not wishing to be bound to any particular theory or mechanism, it is believed that the inner matrix is water soluble, and, when solubilized, the inner matrix diffuses through the outer surface under appropriate conditions as explained in more detail below. The microspheres exhibit a narrow size distribution and have a generally uniform shape. Size distribution is also adjustable by modifying the conditions and reagents used during the preparation process and may be associated with release kinetics as described below. The microspheres are generally less than 10 μm in diameter. See FIG. 13 for a representative size distribution of the microspheres of the invention. The uniform shape of the microspheres is substantially spherical, which is why the microparticles are also referred to herein as "microspheres".

The outer surface of each microsphere is permeable to water and dissolved macromolecules and not only allows aqueous fluids to enter the microsphere, but also allows solubilized macromolecule and polymer to exit the microsphere. The microspheres can be made to release macromolecule and polymer from the interior of the microsphere when placed in an appropriate aqueous medium, such as body fluids or a physiologically acceptable buffer under physiological conditions over a prolonged period of time, thereby providing sustained release of macromolecules. In addition, the microspheres can be made to release macromolecule without an initial burst or rapid release of macromolecule. Sustained release is defined herein as release of macromolecules over an extended period of time. The amount of time over which the macromolecules continue to be released from the microsphere depends on the characteristics of the macromolecule being released and the parameters used to form the microspheres, but in all cases is longer than that of free aqueous diffusion of the macromolecule. Microspheres containing pharmaceutical compounds can be made to release the pharmaceutical compound with the macromolecule and polymer as described above.

As discussed briefly above and in more detail below, the characteristics of the microspheres may be manipulated during preparation by adjusting the type of polymer, polymer concentration, polymer composition, incubation temperature, pH, macromolecule concentration, or the length of time the macromolecule is exposed to the energy source.

The microspheres may be administered to a human or animal by oral or parenteral administration, including intravenous, subcutaneous or intramuscular injection; administration by inhalation; intra articular administration; mucosal administration; ophthalmic administration; and topical administration. Intravenous administration includes catheterization or angioplasty. Administration may be for purposes such as therapeutic and diagnostic purposes as discussed below.

Formation of Microspheres

Microspheres are produced by mixing macromolecules in an aqueous mixture with a water soluble polymer or mixture of polymers to form the microspheres and optionally, thereafter contacting the microspheres with a crosslinking agent and/or an energy source, preferably heat, under conditions sufficient to stabilize the microspheres. The solution is preferably an aqueous solution. Either the macromolecule solution is added to the polymer or the polymer solution is added to the macromolecule solution to cause removal of water from, or dehydration of, the macromolecules. This process is also referred to by those skilled in the art as volume exclusion. Although not wishing to be bound to any particular theory or mechanism, it is believed that the microspheres form during the mixing step; however, such initially formed microspheres are transient and require a further step (e.g., including a crosslinking agent in the mixture and/or by applying heat or other energy source) to stabilize the transiently-formed microspheres.

The pH of the macromolecule-polymer solution is adjusted, either before, after or during the mixing of the polymer with the macromolecule, to a pH near the isoelectric point (pI) of the macromolecule, preferably within 3 to 4 pH units of the pI of the macromolecule, most preferably within 1.5 to 2 pH units of the pI of the macromolecule.

The pH adjustment may be made by adding an acid, base, either in solution or solid form, or a buffer or other pH-adjusting solution or salt, to either the macromolecule solution, the polymer solution, or to the mixture of macromolecule and polymer in accordance with methods well known to those skilled in the art. Preferably the polymer is dissolved in a buffer having a pH near the pI of the macromolecule, and then the pH-adjusted polymer solution is added to the macromolecule, which has been dissolved in an aqueous solution. The pH of the final solution should remain near the pI of the macromolecule.

The macromolecule and polymer solution is then exposed to a crosslinking agent and/or an energy source, such as heat, radiation, or ionization, alone or in combination with sonication, vortexing, mixing or stirring, for a predetermined length of time to stabilize the microspheres. The resulting microspheres are then separated from any unincorporated components present in the solution by physical separation methods well known to those skilled in the art and may then be washed.

The length of incubation time is dependent upon the respective concentrations of polymer and macromolecule and the level of energy of the energy source. Microsphere stabilization can begin to occur immediately upon exposure to the energy source. Preferably, the macromolecule and polymer mixture is heated at a temperature greater than room temperature for between approximately 5 minutes and 24 hours. Most preferably, the polymer and macromolecules are mixed, by stirring or rocking, for 30 minutes at a temperature between approximately 37° C. and 70° C.

Macromolecule

The macromolecule forming the microsphere is any molecule having a tertiary and quaternary structure or capable of having a tertiary and quaternary structure. Most preferably, the macromolecule is a biomolecule such as a protein, including enzymes and recombinant proteins, a peptide, carbohydrate, polysaccharide, carbohydrate- or polysaccharide-protein conjugate, nucleic acid, virus, virus particle, conjugate of a small molecule (such as a hapten) and protein, or mixtures thereof. An organic or inorganic natural or synthetic pharmaceutical compound or drug may be incorporated into the microspheres by attaching the drug to a macromolecule, such as a protein, and then forming the microspheres from the macromolecule-drug complex or conjugate. It will be understood by those skilled in the art that a compound incapable of having a tertiary and quaternary structure can be formed into a microsphere by incorporation or coupling of the compound into a carrier molecule that has a tertiary and quaternary structure. It will be further understood by those skilled in the art that the macromolecule can be a portion of a molecule such as, for example, a peptide, a single-stranded segment of a double-stranded nucleic acid molecule, or a virus particle, having a tertiary and quaternary structure. It will also be understood that the term "macromolecule" includes a plurality of macromolecules and includes combinations of different macromolecules such as a combination of a pharmaceutical compound and an affinity molecule for targeting the pharmaceutical compound to a tissue, organ or tumor requiring treatment. It will be further understood that an affinity molecule can be either the receptor portion or the ligand portion of a receptor-ligand interaction. Examples of ligands that interact with other biomolecules include viruses, bacteria, polysaccharides, or toxins that act as antigens to generate an immune response when administered to an animal and cause the production of antibodies.

Suitable compounds or macromolecules include, but are not limited to, betaxolol™, diclofenac™, doxorubicin, rifampin™, leuprolide acetate, luteinizing hormone releasing hormone (LHRH), (D-Tryp6)-LHRH, nafarelin acetate, insulin, sodium insulin, zinc insulin, protamine, lysozyme, alpha-lactalbumin, basic fibroblast growth factor (bFGF), beta-lactoglobulin, trypsin, carbonic anhydrase, ovalbumin, bovine serum albumin (BSA), human serum albumin (HSA), phosphorylase b, alkaline phosphatase, beta-galactosidase, IgG, fibrinogen, poly-L-lysine, IgM, DNA, desmopressin acetate™, growth hormone releasing factor (GHRF), somatostatin, antide, Factor VIII, G-CSF/GM-CSF, human growth hormone (hGH), beta interferon, antithrombin III, alpha interferon, alpha interferon 2b.

The incubation conditions are typically optimized to incorporate approximately 100% of the macromolecule in the reaction mixture by adjusting the pH, temperature, concentration of macromolecule, or length of reaction or incubation. In general, less energy is required to form microspheres at higher concentrations of macromolecule.

Microspheres composed of nucleic acids are preferably prepared by first mixing the nucleic acid either with a protein, such as bovine serum albumin, or, because nucleic acids are anions, the addition of a cation, such as polylysine, which aids greatly in the formation of microspheres.

As mentioned above, a small molecule or compound incapable of having a tertiary and quaternary structure, such as a peptide or pharmaceutical compound, can be formed into a microsphere by incorporation or coupling of the compound into a carrier molecule that has a tertiary and quaternary structure. This may be achieved in several ways. For example, microspheres may be formed as described herein using a macromolecule having a tertiary and quaternary structure, such as a protein, and then the small molecule or compound is bound inside and/or on the surface of the microsphere. Alternatively, the small molecule or compound is bound to the macromolecule having a tertiary and quaternary structure using hydrophobic or ionic interactions and then microspheres are formed from the macromolecule-small molecule complex using the method described herein. A third way to make microspheres from small molecules is to prepare microspheres using a macromolecule having a tertiary and quaternary structure in such a way that the microsphere has a net charge and then add a small molecule or compound having an opposite net charge so that the small molecule is physically attracted to and remains attached to the microsphere, but can be released over time under the appropriate conditions. Alternatively, different types of non-covalent interactions such as hydrophobic or affinity interactions may be used to allow attachment and subsequent release of small molecules.

When preparing microspheres containing protein, a protein stabilizer such as glycerol, fatty acids, sugars such as sucrose, ions such as zinc, sodium chloride, or any other protein stabilizers known to those skilled in the art may be added prior to the addition of the polymers during microsphere formation to minimize protein denaturation.

Labeled Macromolecule

Prior to being incorporated into a microsphere, the macromolecule may be labeled with a detectable label. The various types of labels and methods of labeling proteins and nucleic acid molecules are well known to those skilled in the art. It will be understood by those skilled in the art that a magnetic substance, such as a metal, is included within the definition of the term label. For example, the macromolecule can be labeled with a metallic substance, such as a metal, so that the microspheres can be separated from other substances in a solution with the aid of a magnetic device.

Several other specific labels or reporter groups are set forth below. For example, the label can be a radiolabel such as, but not restricted to, $^{32}$P, [3] H, [14] C, [35] S, [125] I, or [131] I. A $^{32}$P label can be conjugated to a protein with a conjugating reagent or incorporated into the sequence of a nucleic acid molecule by nick-translation, end-labeling or incorporation of labeled nucleotide. For example, a [3] H, [14] C. or [35] S label can be incorporated into a nucleotide sequence by incorporation of a labeled precursor or by chemical modification, whereas an [125] I or [131] I label is generally incorporated into a nucleotide sequence by chemical modification. Detection of a label can be by methods such as scintillation counting, gamma ray spectrometry or autoradiography.

The label can also be a Mass or Nuclear Magnetic Resonance (NMR) label such as, for example, [13] C., [15] N, or [19]O. Detection of such a label can be by Mass Spectrometry or NMR. Dyes, chemiluminescent agents, bioluminescent agents and fluorogens can also be used to label the macromolecule. Examples of dyes useful for labeling nucleic acids include ethidium bromide, acridine, propidium and other intercalating dyes, and 4', 6'-diamidino-2-phenylindole (DAPI) (Sigma Chemical Company, St. Louis, Mo.) or other nucleic acid stains. Examples of fluorogens include fluorescein and derivatives, phycoerythrin, allophycocyanin, phycocyanin, rhodamine, Texas Red or other fluorogens. The fluorogens are generally attached by chemical modification. The dye labels can be detected by a spectrophotometer and the fluorogens can be detected by a fluorescence detector.

The macromolecule can also be labeled with a chromogen (enzyme substrate) to provide an enzyme or affinity label, or enzyme. Alternatively, the macromolecule can be biotinylated so that it can be utilized in a biotin-avidin reaction, which may also be coupled to a label such as an enzyme or fluorogen. The macromolecule can be labeled with peroxidase, alkaline phosphatase or other enzymes giving a chromogenic or fluorogenic reaction upon addition of substrate.

A label can also be made by incorporating any modified base, amino acid, or precursor containing any label, incorporation of a modified base or amino acid containing a chemical group recognizable by specific antibodies, or by detecting any bound antibody complex by various means including immunofluorescence or immuno-enzymatic reactions. Such labels can be detected using enzyme-linked immunoassays (ELISA) or by detecting a color change with the aid of a spectrophotometer.

Coated Microspheres

Molecules, distinct from the macromolecules of which the microspheres are composed, may be attached to the outer surface of the microspheres by methods known to those skilled in the art to "coat" or "decorate" the microspheres. The ability to attach molecules to the outer surface of the microsphere is due to the high concentration of macromolecule in the microsphere. These molecules are attached for purposes such as to facilitate targeting, enhance receptor mediation, and provide escape from endocytosis or destruction. For example, biomolecules such as phospholipids may be attached to the surface of the microsphere to prevent endocytosis by endosomes; receptors, antibodies or hormones may be attached to the surface to promote or facilitate targeting of the microsphere to the desired organ, tissue or cells of the body; and polysaccharides, such as glucans, may be attached to the outer surface of the microsphere to enhance or to avoid uptake by macrophages.

In addition, one or more cleavable molecules may be attached to the outer surface of or within the microspheres. The cleavable molecules are designed so that the microspheres are first targeted to a predetermined site under appropriate biological conditions and then, upon exposure to a change in the biological conditions, such as a pH change, the molecules are cleaved causing release of the microsphere from the target site. In this way, microspheres are attached to or taken up by cells due to the presence of the molecules attached to the surface of the microspheres. When the molecule is cleaved, the microspheres remain in the desired location, such as within the cytoplasm or nucleus of a cell, and are free to release the macromolecules of which the microspheres are composed. This is particularly useful for drug delivery, wherein the microspheres contain a drug that is targeted to a specific site requiring treatment, and the drug can be slowly released at that site. The preferred site of cleavage is a diester bond.

The microspheres may also be coated with one or more stabilizing substances, which may be particularly useful for long term depoting with parenteral administration or for oral delivery by allowing passage of the microspheres through the stomach or gut without dissolution. For example, microspheres intended for oral delivery may be stabilized with a coating of a substance such as mucin, a secretion containing mucopolysaccharides produced by the goblet cells of the intestine, the submaxillary glands, and other mucous glandular cells.

Additionally, the particles can be non-covalently coated with compounds such as fatty acids or lipids. The coating may be applied to the microspheres by immersion in the solubilized coating substance, spraying the microspheres with the substance or other methods well known to those skilled in the art.

In certain of the preferred embodiments, the microspheres of the invention include a protein and at least one water soluble polymer. As discussed above, the microspheres are formed by contacting the protein and at least one water soluble polymer under aqueous conditions to form the microspheres, and the microspheres are then stabilized by either chemical crosslinking or exposing the microspheres to an energy source, preferably heat, or both, under conditions (e.g., concentration, temperature) which result in microspheres which are resistant to physical and chemical treatments such as sonication and caustic solutions. The particular conditions for forming representative microspheres of the invention are described in the Examples. In the preferred embodiments, the formation reaction is conducted in the absence of the addition of oils or organic solvents.

The protein component of the microsphere may be a carrier protein or a therapeutic protein (see, e.g., Table 1), which represents from about 40 to less than 100% (wt %) of the microsphere.

As used herein, a "carrier protein" refers to a protein which has a molecular weight of at least about 1500 and which exists as a three dimensional structure. The carrier protein can also be a therapeutic protein, i.e., a protein which has a therapeutic activity; however, in general, the phrase "carrier protein" will be used in this application to refer to a protein which has a primary function to provide a three dimensional structure, for the purpose of microsphere formation, even if the carrier protein also may have a secondary function as a therapeutic agent. In certain preferred embodiments, the carrier protein is albumin, particularly, human serum albumin. The protein microspheres of the invention, optionally, further include a therapeutic agent such as a steroid (e.g., estradiol, testosterone, prednisolone, dexamethasone, lidocaine base, procaine base), or any other such chemical entity known to bind to albumin such as GCSF, or paclitaxel. In yet other embodiments (discussed below), the microspheres of the invention further include a complexing agent (preferably, an ionic complexing agent) and, more preferably, a therapeutic agent (preferably a peptide) which is associated with the complexing agent via an ionic or non-ionic interaction. In certain other embodiments, the protein that comprises the matrix is a therapeutic protein (e.g., a hormone such as insulin or human growth hormone) and the microsphere is constructed and arranged to provide sustained release of the therapeutic protein in vivo. More preferably, the microsphere is constructed and arranged to provide sustained release of the therapeutic protein in the absence of significant swelling of the microsphere.

TABLE 1

Proteins
PROTEINS

| CARRIER PROTEINS OR MOLECULES | THERAPEUTIC PROTEINS OR PEPTIDES OR MOLECULES |
|---|---|
| Albumins (preferably, human serum albumin); HAS; BSA; IgG; IgM; insulin; hGH; lysozyme; alpha-lactoglobulin; basic fibroblast growth factor; VEGF; chymotrypsin; trypsin; carbonic anhydrase; ovalbumin; phosphorylase b; alkaline phosphatase; beta-galactosidase; fibrinogen; poly-l-lysine; DNA; immunoglobulins (e.g., antibodies); casein; collagen; soy protein; and gelatin. | Insulin; human growth hormone; GCSF; GMCSF; LHRH; VEGF; basic fibroblast growth factor (bFGF); DNA; RNA; asparaginase; tPA; urokinase; streptokinase; interferon; glucagon; ACTH; oxytocin; secretin; vasopressin; and levothyroxin. |

In general, the microspheres of the invention are formed by mixing the protein together with at least one water soluble polymer under suitable conditions which, preferably, permit the water soluble polymer to remove water from ("dehydrate") the protein (see e.g., Table 2) within specified or preferred ratios (wt/wt) of protein to water soluble polymer (e.g., ratios range from about 1 protein: 1 polymer to about 1 protein: 1000 polymer). The preferred ratio of protein to water soluble polymer in the microsphere formation reaction is in the range from about 1 protein: 5 polymer to about 1 protein: 30 polymer. As noted above, a "water soluble polymer" of the invention refers to a polymer or mixture of polymers which, preferably, are capable of interacting with the macromolecule (e.g., protein or other molecule) to cause volume exclusion. Thus, the preferred process involves using an entirely aqueous system with no oil or organic solvents involved.

Suitable water soluble polymers include soluble linear or branched polymers, preferably those having a high molecular weight. Polymers can be highly water soluble, moderately-water soluble, or slightly water soluble (greater than 2% wt/vol water soluble). The preferred water soluble polymers are water soluble or soluble in a water miscible solvent. The water soluble polymers may be solubilized by first being dissolved in a water miscible solvent and then combining the polymer solution with an aqueous solvent. In the particularly preferred embodiments, the water soluble polymers of the invention are selected from water soluble polymers identified in Table 2. In the particularly preferred embodiments, the water soluble polymer is a carbohydrate-based polymer.

The preferred polymer is polyvinylpyrrolidone, polyethylene glycol, dextran, polyoxyethylene-polyoxypropylene copolymer, polyvinyl alcohol, starch, hetastarch, or mixtures thereof, the characteristics of which are described in more detail below. The polymer or polymer mixture may be prepared in accordance with the methods set forth in U.S. Pat. No. 5,525,519 to James E. Woiszwillo, or PCT Patent Application No. US93-00073 (International Publication No.

WO 93/14110), filed Jan. 7, 1993 and published on Jul. 22, 1993 by James E. Woiszwillo, both of which are incorporated herein by reference), in which the polymer is dissolved in water or an aqueous solution, such as a buffer, in a concentration between approximately 1 and 50 g/100 ml depending on the molecular weight of the polymer. The preferred total polymer concentration in the polymer solution is between 10% and 80%, expressed as weight/volume percent. The preferred concentration of each polymer in the polymer solution is between 5% and 50%. As discussed above, the pH of the polymer solution may be adjusted before being combined with the macromolecule so that the addition of the polymer causes a pH adjustment of the macromolecule solution, most preferably within one pH unit of the pI. The pH may be adjusted during the preparation of the polymer solution by preparing the polymer in a buffer having a predetermined pH. Alternatively, the pH may be adjusted after preparation of the polymer solution with an acid or a base.

Polyoxyethylene-polyoxypropylene copolymer, also known as poloxamer, is sold by BASF (Parsippany, N.J.) and is available in a variety of forms with different relative percentages of polyoxyethylene and polyoxypropylene within the copolymer.

PVP is a non-ionogenic, hydrophilic polymer having a mean molecular weight ranging from approximately 10,000 to 700,000 and the chemical formula $(C_6H_9NO)[n]$. PVP is also known as poly[1-(2-oxo-1 -pyrrolidinyl)ethylene], Povidone™, Polyvidone™, RP 143™, Kollidon™, Peregal ST™, Periston™, Plasdone™, Plasmosan™, Protagent™, Subtosan™, and Vinisil™. PVP is non-toxic, highly hygroscopic and readily dissolves in water or organic solvents.

Polyethylene glycol (PEG), also known as poly (oxyethylene) glycol, is a condensation polymer of ethylene oxide and water having the general chemical formula $HO(CH_2CH_2O)[n]H$.

TABLE 2

Water soluble polymers
WATER SOLUBLE POLYMERS 1) carbohydrate-based polymers, such as methylcellulose, carboxymethyl cellulose-based polymers, dextran, polydextrose, derivatized chitins, chitosan, and starch (including hetastarch), and derivatives thereof, 2) polyaliphatic alcohols such as polyethylene oxide and derivatives thereof including polyethylene glycol (PEG), PEG-acrylates, polyethylene imine, polyvinyl acetate, and derivatives thereof; 3) poly(vinyl) polymers such as poly(vinyl) alcohol, poly(vinyl)pyrrolidone, poly(vinyl)phosphate, poly(vinyl)phosphonic acid, and derivatives thereof, 4) polyacrylic acids and derivatives thereof; 5) polyorganic acids, such as polymaleic acid, and derivatives thereof, 6) polyamino acids, such as polylysine, and polyimino acids, such as polyimino tyrosine, and derivatives thereof; 7) co-polymers and block co-polymers, such as poloxamer 407 or Pluronic L-101 TM polymer, and derivatives thereof; 8) tert-polymers and derivatives thereof; 9) polyethers, such as poly(tetramethylene ether glycol), and derivatives thereof; 10) naturally occurring polymers, such as zein and pullulan, and derivatives thereof, 11) polyimids, such as polyn-tris(hydroxymethyl)methylmethacrylate, and derivatives thereof, 12) surfactants, such as polyoxyethylene sorbitan, and derivatives thereof, 13) polyesters such as poly(ethylene glycol)(n)monomethyl ether mono(succinimidylsuccinate)ester, and derivatives thereof; 14) branched and cyclo-polymers, such as branched PEG and cyclodextrins, and derivatives thereof; and 15) polyaldehydes, such as poly(perfluoropropylene oxide-b-perfluoroformaldehyde), and derivatives thereof.

Dextran is a term applied to polysaccharides produced by bacteria growing on a sucrose substrate. Native dextrans produced by bacteria such as Leuconostoc mesenteroides and Lactobacteria dextranicum usually have a high molecular weight. Dextrans are routinely available and are used in injectable form as plasma expanders in humans.

Polyvinyl alcohol (PVA) is a polymer prepared from polyvinyl acetates by replacement of the acetate groups with hydroxyl groups and has the formula $(CH_2CHOH)[n]$. Most polyvinyl alcohols are soluble in water.

PEG, dextran, PVA and PVP are commercially available from chemical suppliers such as the Sigma Chemical Company (St. Louis, Mo.).

Most preferably, the polymer is a polymer mixture containing an aqueous solution of PVP having a molecular weight between 10,000 and 360,000, most preferably 40,000, and PEG having a molecular weight between 200 and 35,000. PVP having a molecular weight of 40,000 and PEG having a molecular weight of 3500 is preferred. Preferably, the PVP is dissolved in an acetate buffer and PEG is added to the aqueous PVP solution. The concentration of each polymer is preferably between 1 and 40 g/100 ml depending of the molecular weight of each polymer. Equal concentrations of PVP and PEG generally provide the most favorable polymer mixture for the formation of microspheres.

An alternative preferred polymer is a dextran, having a molecular weight from approximately 3000 to 500,000 daltons.

The volume of polymer added to the macromolecule varies depending on the size, quantity and concentration of the macromolecule. Preferably, two volumes of the polymer mixture at a 5–50% total polymer concentration are added to one volume of a solution containing the macromolecule. The polymer is present in a liquid phase during the reaction with macromolecule.

In certain of the embodiments and, in particular, the embodiments of the microspheres which do not further contain a complexing agent, the water soluble polymer preferably is not PEG, PVP, dextran, nonylphenol-ethoxylates, and/or polyvinyl alcohol.

Complexing Agents

According to another aspect of the invention, a microsphere further including a complexing agent is provided. As used herein, a complexing agent refers to a molecule which is capable of facilitating loading, retaining and/or otherwise delaying the release of the therapeutic agent from the microsphere (see, e.g., Table 3). In certain embodiments, the microsphere of this aspect includes: (1) a macromolecule such as a protein (e.g., albumin, as described above); (2) at least one water soluble polymer (e.g., hetastarch, PEG/PVP, as described above); and (3) a complexing agent.

TABLE 3

Complexing Agents
COMPLEXING AGENTS

| IONIC | | OTHER INTERACTION (including non-ionic and mixed ionic and non-ionic |
|---|---|---|
| POLYANIONIC | POLYCATIONIC | interactions) |
| Dextran sulfate | Poly-lysine | Albumin |
| Heparin sulfate | Poly arginine | IgG |
| Heparan sulfate | Poly imino acids | IgM |
| Chondroitin sulfate | Poly imino tyrosine | hydrophobic polymers |
| Na polystyrene sulfonate | Cholestyramine resin | silicone |
| Carboxymethylcellulose | Diethyl amino ethyl cellulose | zein |
| Poly aspartic acid | | Lignin |

TABLE 3-continued

Complexing Agents
COMPLEXING AGENTS

| IONIC | | OTHER INTERACTION (including non-ionic and mixed ionic and non-ionic interactions) |
|---|---|---|
| POLYANIONIC | POLYCATIONIC | |
| Poly glutamic acid | Poly citrulline<br>Poly ornithine | fatty acids<br>phospholipids<br>gelatin<br>divalent cations (e.g., calcium, magnesium, zinc) |

In certain particularly preferred embodiments of this aspect of the invention, the microspheres include: (1) a carrier protein; (2) a water soluble polymer; (3) a first complexing agent that is a polyanionic polysaccharide such as dextran sulfate, galacturonic acids, alginates, mannuronic acid, guluronic acid, hyaluronic acid, chondroitin sulfates, heparin, chitin, chitosan, glycosaminoglycans, proteoglycans) and cationic complexing agents (i.e., complexing agents having a positive charge); and (4) a second complexing agent that is a divalent metal cation selected from the group consisting of calcium, magnesium, zinc, strontium, barium, manganese, and iron. In the preferred embodiments of this aspect, the carrier protein is an albumin or an immunoglobulin or other protein selected from the group consisting of the carrier proteins of Table 1. In general, the microspheres of this aspect of the invention contain from about 40 to less than 100% protein. In the preferred embodiments of this aspect, the water soluble polymer is selected from the group consisting of the water soluble polymers of Table 2, preferably a carbohydrate-based polymer, and more preferably, a hydroxyethylstarch.

As with other aspects of the invention, these microspheres preferably have a smooth surface which includes a plurality of channel openings that are less than 1000 angstroms as determined by gas adsorption technique for pore sizing and, preferably, do not contain detectable oil or organic solvent.

A preferred method of incorporating an ionic complexing agent(s) is to combine the ionic complexing(s) with a water soluble polymer in aqueous solution and the protein in aqueous solution and stabilize the microsphere with heat or with crosslinking agents.

In general, the complexing agent is an ionic complexing agent (i.e., the complexing agent is capable of an ionic interaction or a non-ionic complexing agent (i.e., the complexing agent is capable of a non-ionic (e.g., hydrophobic) interaction or an agent with both ionic and nonionic interactions (e.g., IgG). Exemplary non-ionic complexing agents and ionic complexing agents such as anionic complexing agents (i.e., complexing agents having a negative charge) and cationic complexing agents (i.e., complexing agents having a positive charge) are provided in Table 3.

In certain embodiments, the complexing agent is an anionic complexing agent having the structure of formula I:

POLY-[Y<sup>−</sup>]<sub>n</sub> X<sup>+</sup>   I.

wherein POLY represents a principal chain of the anionic complexing agent which may be linear or branched;
wherein Y<sup>−</sup> represents an anionic group, e.g., sulfates, carboxyls, phosphates, nitrates, carbonates and the like, that may be coupled to any one or more of the branches of the principal chain;
wherein X<sup>+</sup> represents a cationic group, e.g., that is a counter ion to the anionic group;
wherein n is an integer from 1 to 10,000, preferably, from 5 to 100 and, more preferably, from 5 to 1000, and still more preferably, from 5 to 10,000; and
wherein when n is greater than 1, the n Y<sup>−</sup> groups can be the same or different.

In yet other embodiments of the invention the complexing agent is a cationic complexing agent having the structure of formula II:

POLY-[X<sup>+</sup>]<sub>n</sub> Y<sup>−</sup>   II.

wherein POLY represents a principal chain of the cationic complexing agent which may be linear or branched;
wherein X<sup>+</sup> represents a cationic group, e.g., an amino group, that may be coupled to any one or more of the branches of the principal chain;
wherein Y<sup>−</sup> represents an anionic group, that is a counter ion to the cationic group;
wherein n is an integer from 1 to 10000, preferably, from 5 to 100 and, more preferably, from 5 to 1000, and most preferably, from 5 to 10,000; and
wherein when n is greater than 1, the n X<sup>−</sup> groups can be the same or different.

Active Agents

According to another aspect of the invention, a microsphere further including an active agent is provided. Exemplary categories of active agents are provided in Table 4.

TABLE 4

Therapeutic Agents: Categories
THERAPEUTIC AGENTS-CATEGORIES hormones, antibiotics and other antiinfective agents, hematopoietics, thrombopoietics, agents, antidementia agents, antiviral agents, antitumoral agents (chemotherapeutic agents), antipyretics, analgesics, antiinflammatory agents, antiulcer agents, antiallergic agents, antidepressants, psychotropic agents, cardiotonics, antiarrythmic agents, vasodilators, antihypertensive agents such as hypotensive diuretics, antidiabetic agents, anticoagulants, cholesterol lowering agents, therapeutic agents for osteoporosis, enzymes, vaccines, immunological agents and adjuvants, cytokines, growth factors, nucleotides and nucleic acids; carbohydrates and polysaccharides; viruses and virus particles; conjugates or complexes of small molecules and proteins, or mixtures thereof; and organic or inorganic synthetic pharmaceutical drugs The microspheres into which the active agent can be loaded may include a complexing agent to facilitate loading and/or modify the release of the active agent from the microsphere. Alternatively, the active agent can be loaded into the above-described microspheres which lack a complexing agent, e.g., the protein and/or the water soluble polymers of the invention can interact with the active agent to facilitate loading and/or modify its release from the microsphere. In general, although the active agent can be loaded into a microsphere of the invention during preparation of the microsphere, it is preferable to load the active agent into a preformed microsphere of the invention and, more preferable to load the active agent into a preformed microsphere which contains a complexing agent(s) to facilitate loading and/or sustained release of the agent. In contrast to hydrogel microspheres, the microspheres of the invention do not swell significantly in water and, further, the stabilized microspheres do not require swelling in order to provide sustained release of the therapeutic protein and/or physiologically active agent from the microsphere.

As used herein, an active agent refers to an agent which has a diagnostic or therapeutic activity. Accordingly, an active agent optionally includes a detectable label (e.g., a radioactive label) that is useful for identifying the locations of the released agent in vivo; Active agents also include therapeutic agents which are useful for treating a disease or condition. In certain embodiments, the preferred physiologically active agents are protein or peptide agents. Such protein or peptide agents typically can be further divided into categories, based upon the activity of the agent or the type of disease or condition that is being treated. The physiologically active agent which can be used in the present invention includes but is not limited to categories of antibiotics, hematopoietic agents, antiinfective agents, antidementia agents, antiviral agents, antitumoral agents, antipyretics, analgesics, antiinflammatory agents, antiulcer agents, antiallergic agents, antidepressants, psychotropic agents, cardiotonics, antiarrythmic agents, vasodilators, antihypertensive agents such as hypotensive diuretics, antidiabetic agents, anticoagulants, cholesterol lowering agents, therapeutic agents for osteoporosis, hormones, vaccines and so on (see, e.g., Table 4). While specific examples of active agents (e.g., peptide and non-peptide agents) for use in accordance with this invention are mentioned below, this does not mean that other peptide or non-peptide agents are excluded. These active agents may be naturally occurring, recombinant or chemically synthesized substances.

The physiologically active agents of the invention include protein or peptide agents, as well as non-protein or non-peptide agents. For ease of discussion, such protein or peptide agents are referred to collectively herein as peptide agents; non-protein and non-peptide agents shall be referred to collectively herein as non-peptide agents. Exemplary non-peptide agents include the following non-limiting categories of agents: a) nucleotides and nucleic acids; b) carbohydrates and polysaccharides; c) viruses and virus particles; d) conjugates or complexes of small molecules and proteins, or mixtures thereof; and e) organic or inorganic natural or synthetic pharmaceutical drugs. A further description of these and other agents that can be used in accordance with the methods and compositions of the present invention are described in U.S. Pat. Nos. 5,482,706; 5,514,670; and 4,357,259, the entire contents of which are incorporated herein by reference.

The preferred physiologically active peptide agents include peptide hormones, cytokines, growth factors, factors acting on the cardiovascular system, factors acting on the central and peripheral nervous systems, factors acting on humoral electrolytes and hemal organic substances, factors acting on bone and skeleton, factors acting on the gastrointestinal system, factors acting on the immune system, factors acting on the respiratory system, factors acting on the genital organs, and enzymes.

Exemplary hormones include insulin, growth hormone, parathyroid hormone, luteinizing hormone-releasing hormone (LH-RH), adrenocorticotropic hormone (ACTH), amylin, oxytocin, luteinizing hormone, (D-Tryp6)-LHRH, nafarelin acetate, leuprolide acetate, follicle stimulating hormone, glucagon, prostaglandins, PGE1, PGE2 and other factors acting on the genital organs and their derivatives, analogs and congeners. As analogs of said LH-RH, such known substances as those described in U.S. Pat. Nos. 4,008,209, 4,086,219, 4,124,577, 4,317,815 and 5,110,904 can be mentioned.

Exemplary antibiotics include tetracycline, aminoglycosides, penicillins, cephalosporins, sulfonamide drugs, chloramphenicol sodium succinate, erythromycin, vancomycin, lincomycin, clindamycin, nystatin, amphotericin B, amantidine, idoxuridine, p-amino salicyclic acid, isoniazid, rifampin, antinomycin D, mithramycin, daunomycin, adriamycin, bleomycin, vinblastine, vincristine, procarbazine, imidazole carboxamide.

Exemplary hematopoietic or thrombopoietic factors include, among others, erythropoietin, granulocyte colony stimulating factor (G-CSF), granulocyte-macrophage stimulating factor (GM-CSF) and macrophage colony stimulating factor (M-CSF), leukocyte proliferation factor preparation (Leucoprol, Morinaga Milk), thrombopoietin, platelet proliferation stimulating factor, megakaryocyte proliferation (stimulating) factor, and factor VIII.

Exemplary antidementia agents include selegelene.

Exemplary antiviral agents include amantidine and protease inhibitors.

Exemplary antitumoral agents include doxorubicin, Daunorubicin, taxol, and methotrexate. Exemplary antipyretics and analgesics include aspirin, Motrin, Ibuprofin, naprosyn, Indocin, and acetaminophen.

Exemplary antiinflammatory agents include NSAIDS, aspirin, steroids, dexamethasone, hydrocortisone, prednisolone, and Diclofenac Na.

Exemplary antiulcer agents include famotidine, cimetidine, nizatidine, ranitidine, and sucralfate.

Exemplary antiallergic agents include antihistamines, diphenydramine, loratadine, and chlorpheniramine.

Exemplary antidepressants and psychotropic agents include lithium, amitryptaline, tricyclic antidepressants, fluoxetine, prozac, and paroxetine.

Exemplary cardiotonics include digoxin.

Exemplary antiarrythmic agents include metoprolol and procainamide.

Exemplary vasodilators include nitroglycerin, nifedipine, and Isosorbide dinitrate.

Exemplary diuretics include hydrochlorothiazide and furosemide.

Exemplary antihypertensive agents include captopril, nifedipine, and atenolol.

Exemplary antidiabetic agents include glucozide, chloropropamide, metformin, and insulin.

Exemplary anticoagulants include warfarin, heparin, and Hirudin.

Exemplary cholesterol lowering agents include lovastatin, cholestyamine, and clofibrate.

Exemplary therapeutic agents for treating osteoporosis and other factors acting on bone and skeleton include calcium, alendronate, bone GLa peptide, parathyroid hormone and its active fragments (osteostatin, Endocrinology 129, 324, 1991), histone H4-related bone formation and proliferation peptide (OGP, The EMBO Journal 11, 1867, 1992) and their muteins, derivatives and analogs thereof.

Exemplary enzymes and enzyme cofactors include: pancrease, L-asparaginase, hyaluronidase, chymotrypsin, trypsin, tPA, streptokinase, urokinase, pancreatin, collagenase, trypsinogen, chymotrypsinogen, plasminogen, streptokinase, adenyl cyclase, and superoxide dismutase (SOD).

Exemplary vaccines include Hepatitis B, MMR (measles, mumps, and rubella), and Polio vaccines.

Exemplary immunological adjuvants include: Freunds adjuvant, muramyl dipeptides, concanavalin A, BCG, and levamisole.

Exemplary cytokines include lymphokines, monokines, hematopoietic factors and so on. Lymphokines and cytokines useful in the practice of the invention include interferons (e.g., interferon—alpha, —beta and—gamma ), interleukins (e.g. interleukin 2 through 11) and so on. Monokines useful in the practice of the invention include interleukin-1, tumor necrosis factors (e.g. TNF—alpha and—beta), malignant leukocyte inhibitory factor (LIF) and so on.

Exemplary growth factors include nerve growth factors (NGF, NGF-2/NT-3), epidermal growth factor (EGF), fibroblast growth factor (FGF), insulin-like growth factor (IGF), transforming growth factor (TGF), platelet-derived cell growth factor (PDGF), hepatocyte growth factor (HGF) and so on.

Exemplary factors acting on the cardiovascular system include factors which control blood pressure, arteriosclerosis, etc., such as endothelins, endothelin inhibitors, endothelin antagonists described in EP 436189, 457195, 496452 and 528312, JP [Laid Open] No. H-3-94692/1991 and 130299/1991, endothelin producing enzyme inhibitors vasopressin, renin, angiotensin I, angiotensin II, angiotensin III, angiotensin I inhibitor, angiotensin II receptor antagonist, atrial naturiuretic peptide (ANP), antiarrythmic peptide and so on.

Exemplary factors acting on the central and peripheral nervous systems include opioid peptides (e.g. enkephalins, endorphins), neurotropic factor (NTF), calcitonin gene-related peptide (CGRP), thyroid hormone releasing hormone (TRH), salts and derivatives of TRH [JP [Laid Open] No. 50-121273/1975 (U.S. Pat. No. 3,959,247), JP [Laid Open] No. 52-116465/1977 (U.S. Pat. No. 4,100,152)], neurotensin and so on.

Exemplary factors acting on the gastrointestinal system include secretin and gastrin.

Exemplary factors acting on humoral electrolytes and hemal organic substances include factors which control hemaglutination, plasma cholesterol level or metal ion concentrations, such as calcitonin, apoprotein E and hirudin. Laminin and intercellular adhesion molecule 1 (ICAM 1) represent exemplary cell adhesion factors.

Exemplary factors acting on the kidney and urinary tract include substances which regulate the function of the kidney, such as brain-derived naturiuretic peptide (BNP), urotensin and so on.

Exemplary factors which act on the sense organs include factors which control the sensitivity of the various organs, such as substance P.

Exemplary factors acting on the immune system include factors which control inflammation and malignant neoplasms and factors which attack infective microorganisms, such as chemotactic peptides and bradykinins.

Exemplary factors acting on the respiratory system include factors associated with asthmatic responses.

Also included are naturally occurring, chemically synthesized or recombinant peptides or proteins which may act as antigens, such as cedar pollen and ragweed pollen. These factors are administered, either independently, coupled to haptens, or together with an adjuvant, in the formulations according to the present invention.

Microsphere Formation, Stabilization, and Characterization

The method for forming the microspheres of the invention involves: (1) combining, in one or more aqueous solutions, a macromolecule such as a protein, a water soluble polymer (e.g., carbohydrate-based polymer) and a complexing agent (s) to form an aqueous mixture (either as a single or multi-phase system); and, preferably, (2) subjecting the aqueous mixture to a crosslinking agent (e.g., EDC [1-ethyl-3-(3-dimethylamino-propylcarbodiimide]) and/or an energy source for a time sufficient to form a microsphere, particularly, a microsphere having a smooth surface which includes a plurality of channel openings that are less than 1000 angstroms in diameter as determined by gas adsorption technique for pore sizing. Exemplary methods of preparing the microspheres are provided in the Examples.

The particularly preferred embodiments are microspheres which include:

(1) a carrier protein;
(2) a water soluble polymer;
(3) a first complexing agent that is a poly anionic polysaccharide; and
(4) a second complexing agent that is a divalent metal cad ion, preferably calcium or magnesium. Active agents, such as therapeutic agents or diagnostic agents, can be introduced into these microspheres following their formation. The preferred method for forming these particularly preferred embodiments of the invention involves: (1) combining, essentially simultaneously, in one or more aqueous solutions, the carrier protein, the water soluble polymer, the first complexing agent, and the second complexing agent to form an aqueous mixture; and (2) allowing the microspheres to form. Optionally, the microspheres can be further subjected to a cross-linking agent to further stabilize the microspheres. By "essentially simultaneously," it is meant that the second complexing agent (preferably calcium or magnesium) is added within about 30 minutes of the addition of the other forming components. Applicants have discovered that the addition of calcium or magnesium to the aqueous mixture which is not an essentially simultaneous addition results in the formation of aggregates and other amorphous forms of particles, rather than the spherically shaped microspheres which are formed when the calcium or magnesium is combined essentially simultaneously with the other components during the microsphere formation process.

Microspheres can be stabilized by incubation of the formed microspheres in the presence of a crosslinking agent and/or an energy source (e.g., heat) for a predetermined length of time. Exemplary crosslinking agents include dialdehydes, amines, multivalent ions, multifinctional molecules having an affinity for specific reactive groups on the macromolecule being crosslinked, N-substituted maleimides, bifinctional alkyl halides, aryl halides, isocyanates, aliphatic or aromatic dicarboxylic acids, aliphatic or aromatic disulphonic acids, bifunctional imidoesters, and vinylsulphones. Additional crosslinking agents and methods for using same to stabilize a microsphere are described in U.S. Pat. No. 5,578,709, issued to J. Woiszwillo, the entire contents of which are incorporated in their entirety herein by reference. The preferred energy source is heat. However, it will be understood by those skilled in the art that other energy sources include heat, radiation, and ionization, alone or in combination with sonication, vortexing, mixing or stirring. Microsphere formation and/or stabilization can occur immediately upon exposure to the energy source or may require an extended exposure to the energy source depending on the characteristics of the components and conditions. Preferably, the macromolecule-polymer solution mixture, is incubated in a water bath at a temperature greater than or equal to 37° C. and less than or equal to 90° C. for between approximately 5 minutes and 2 hours. Most preferably, the mixture is incubated for 5–30 minutes at a temperature between 50° C. and 90° C. It should be noted that microspheres may be formed at lower temperatures by utilizing a higher macromolecule concentration. The maximum incubation temperature is determined by the characteristics of the macromolecule and the ultimate function of the microsphere. For example, for a microsphere in which the macromolecule is a protein, a temperature less than approximately 70° C. is preferred to retain protein activity.

The formed microspheres are separated from the non-incorporated components of the incubation mixture by conventional separation methods well known to those skilled in the art. Preferably, the incubation mixture is centrifuged so that the microspheres sediment to the bottom of the centrifuge tube and the non-incorporated components remain in the supernatant, which is then removed by decanting. Alternatively, a suspension containing formed microspheres is filtered so that the microspheres are retained on the filter and the non-incorporated components pass through the filter.

Further purification of the microspheres is achieved by washing in an appropriate volume of a washing solution. The preferred washing solution is a buffer, most preferably a nonionic aqueous solution or a nonionic aqueous solution containing water soluble polymers. Repeated washings can be utilized as necessary and the microspheres separated from the wash solution as described above.

As mentioned above, the characteristics of the microspheres can be altered by manipulating the incubation conditions. For example, the release kinetics of the microspheres may be retarded by increasing the reaction temperature or extending the length of reaction time during microsphere formation. Release kinetics are also manipulated by choosing different polymers, different concentrations of polymers, or different ratios of polymers used in the formation of the microspheres.

Microsphere size, shape and release kinetics can also be controlled by adjusting the microsphere formation conditions. For example, particle formation conditions can be optimized to produce smaller or larger particles or the overall incubation time or incubation temperature can be increased, resulting in particles which have prolonged release kinetics.

Nucleic Acid Microspheres

According to still other embodiments of the invention, microspheres in which the macromolecule is a nucleic acid are provided. The nucleic acid-containing microspheres include: (1) a nucleic acid (e.g., plasmid, viral vector, oligonucleotide, RNA, antisense and missense nucleic acids); (2) a polycationic polymer(s) (e.g., polylysine); and (3) a water soluble polymer (as described above). Thus, according to a related aspect of the invention, a method for forming the nucleic acid-containing microspheres is provided. The method involves: (1) combining, in one or more aqueous solutions, a nucleic acid(s), a polycationic polymer (s) and a water soluble polymer(s) to form an aqueous mixture; and (2) subjecting the aqueous mixture to a crosslinking agent and/or an energy source for a time sufficient to form a microsphere. Exemplary methods of forming the nucleic acid microspheres are provided in the Examples.

Pharmaceutical Compositions

According to yet another aspect of the invention, a pharmaceutical composition of matter and method for producing same are provided. The composition includes a container containing a single dose of microspheres containing an active agent for treating a condition that is treatable by the sustained release of an active agent from the microspheres. The number of microspheres in the single dose is dependent upon the amount of active agent present in each microsphere and the period of time over which sustained release is desired. Preferably, the single dose is selected to achieve the sustained release of the active agent over a period of about 1 to about 180 days with the desired release profile.

According to another aspect of the invention, a syringe-containing composition is provided. The composition includes a syringe containing a single dose of microspheres containing an active agent for treating a condition that is treatable by the sustained release of the active agent form the microspheres; and a needle attached to the syringe, wherein the needle has a bore size that is from 14 to 30 gauge.

Remarkably, the preferred microspheres of the invention can be prepared to have a dimension which permits the delivery of microspheres using a needleless syringe (MediJector, Derata Corporation, Minneapolis, Minn. 55427), thereby eliminating the disposal problems inherent to needles which must be disposed as a biohazard waste product. Thus, according to a particularly preferred aspect of the invention, a needleless syringe containing one or more doses of microspheres containing an active agent for treating a condition is provided. The microspheres can be prepared to have qualities suitable to be delivered by other parenteral and non-parenteral routes such as oral, buccal, intrathecal, nasal, pulmonary, transdermal, transmucosal and the like.

Utilities

In summary, the compositions of the invention can be thought of as combining various components, as exemplified in the Tables, under conditions to form microspheres which, preferably, having desirable smooth surface characteristics that are quantifyable in terms of determining whether the microspheres have formed (e.g., by visual detection) and in terms of determining the diameter of the microsphere channel openings. Thus, in certain of its broadest aspect, the compositions of the invention are directed to microspheres having the requisite channel opening dimensions and comprising a macromolecule (preferably a protein of Table 1) and a water soluble polymer (preferably a polymer of Table 2). In yet another aspect, the microspheres comprise a macromolecule (preferably a protein of Table 1), a water soluble polymer (preferably a polymer of Table 2), and a complexing agent (preferably of Table 3). In the particularly preferred embodiments, the microspheres include: (1) a carrier protein; (2) a water soluble polymer; (3) a first complexing agent that is a polyanionic polysaccharide; and (4) a second complexing agent that is a divalent metal cation selected from the group consisting of calcium and magnesium. In still further aspects, the invention is directed to any of these aspects wherein the microspheres further comprise a therapeutic agent (preferably of Table 4). Thus, in certain embodiments of these aspects, a protein(s) of Table 1 is combined with a water soluble polymer(s) of Table 2 and an active agent(s) of Table 4. In yet other embodiments of these aspects, a nucleic acid(s) is combined with a polycation(s) of Table 3, a water soluble polymer(s) of Table 2 and, optionally, a therapeutic agent(s) of Table 4. Accordingly, the methods of the invention provide various microspheres which can be designed for different therapeutic and diagnostic applications by selecting the appropriate combination of agents for achieving the therapeutic or diagnostic goal.

When used therapeutically, the microspheres of the invention are administered in therapeutically effective amounts. In general, a therapeutically effective amount means that amount of active agent necessary to delay the onset of, inhibit the progression of, or halt altogether the particular condition being treated. Generally, a therapeutically effective amount will vary with the subject's age, condition, and sex, as well as the nature and extent of the disease in the subject, all of which can be determined by one of ordinary skill in the art. The dosage may be adjusted by the individual physician or veterinarian, particularly in the event of any complication. A therapeutically effective amount of active agent typically varies from 0.01 mg/kg to about 1000 mg/kg, preferably from about 0.1 mg/kg to about 200 mg/kg, and most preferably from about 0.2 mg//kg to about 20 mg/kg, in one or more dose administrations daily, for one or more days, weekly, monthly, every two or three months, and so forth.

The microspheres may be administered alone or in combination with other drug therapies as part of a pharmaceutical composition. Such a pharmaceutical composition may include the microspheres in combination with any standard physiologically and/or pharmaceutically acceptable carriers which are known in the art. The compositions should be sterile and contain a therapeutically effective amount of the microsphere in a unit of weight or volume suitable for administration to a patient. The term "pharmaceutically-acceptable carrier" as used herein means one or more compatible solid or liquid filler, diluents or encapsulating substances which are suitable for administration into a human or other animal. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy. Pharmaceutically acceptable further means a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, desiccants, bulking agents, propellants, acidifying agents, coating agents, solubilizers, and other materials which are well known in the art. Carrier formulations suitable for oral, subcutaneous, intravenous, intramuscular, etc. administrations can be found in Remington's Pharmaceutical Sciences, Mack Publishing Co., Easton, Pa.

A variety of administration routes are available. The particular mode selected will depend, of course, upon the particular drug selected, the severity of the condition being treated, and the dosage required for therapeutic efficacy. The methods of the invention, generally speaking, may be practiced using any mode of administration that is medically acceptable, meaning any mode that produces effective levels of the active compounds without causing clinically unacceptable adverse effects. Such modes of administration include oral, rectal, topical, nasal, interdermal, or parenteral routes. The term "parenteral" includes subcutaneous, intravenous, intramuscular, or infusion. Oral administration will be preferred for prophylactic treatment because of the convenience to the patient as well as the dosing schedule.

The pharmaceutical compositions may conveniently be presented in unit dosage form and may be prepared by any of the methods well-known in the art of pharmacy. All methods include the step of bringing the microsphere into association with a carrier which constitutes one or more accessory ingredients. In general, the compositions are prepared by uniformly and intimately bringing the microspheres into association with a liquid carrier, a finely divided solid carrier, or both, and then, if necessary, shaping the product.

Preparations for parenteral administration include sterile aqueous or non-aqueous solutions, suspensions, and emulsions. Additional examples of solvents include propylene glycol, polyethylene glycol, vegetable oils such as olive oil, and injectable organic esters such as ethyl oleate. Aqueous carriers include water, salts and buffer solutions such as saline and buffered media, alcoholic/aqueous solutions and emulsions or suspensions. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. In general, the microspheres can be administered to the subject (any mammalian recipient) using the same modes of administration that currently are used for microparticle therapy in humans.

The microspheres are useful for a wide variety of separations, diagnostic, therapeutic, industrial, commercial, cosmetic, and research purposes as discussed in more detail below. For example, for in vivo diagnostic purposes, the microspheres can include a macromolecule such as an immunoglobulin or cell receptor labeled with a detectable label. Administration of the labeled microsphere to a patient creates an imaging agent for the diagnosis of a proliferative disorder such as cancer or a tool for the evaluation of the success of a therapeutic agent in reducing the proliferation of a particular adverse cell or organism.

For in vitro diagnosis, microspheres containing a macromolecule, such as an immunoglobulin, cell receptor or oligonucleotide probe specific for the cell or organism under investigation, are combined with a test sample, the microspheres are separated from any non-bound components of the sample, and bound molecules are detected by conventional methods.

The microspheres are useful as therapeutic agents and may enable the use of alternative routes of administration when the microspheres include a therapeutic drug and are administered to a patient for slow release or targeted delivery of the drug to the site requiring therapy. The microspheres are also useful as therapeutic or prophylactic agents when the microspheres include a macromolecule that is itself a therapeutic or prophylactic agent, such as an enzyme or immunoglobulin. The slow release of such therapeutic agents is particularly useful for therapeutic proteins or peptides having short half-lives that must be administered by injection.

The microspheres are also useful for the purification of molecules from a complex mixture, as a reagent for the detection or quantification of a specific molecule, or for the production of molecules, such as antibodies. For example, microspheres containing a macromolecule, such as an immunoglobulin, can be attached to a chromatography column and used in immunoaffinity chromatography to separate a ligand from a complex mixture. Alternatively, microspheres including a labeled macromolecule or a mixture of labeled macromolecules specific for different cells or biomolecules, such as cell receptors, can be used to detect changes in the number of cells or biomolecules in response to a particular test condition using techniques such as flow cytometry.

Furthermore, the microspheres can be used as adjuvants for vaccine production wherein antigen-containing microspheres are injected into a research animal, such as a mouse or rabbit, to trigger an enhanced immune response for the production of antibodies to the antigen.

Additional commercial uses include cleaning formulations, such as the formation of enzyme particles for addition to detergents; cosmetics, such as the formation of collagen particles to be suspended in a lotion or cream; ink; and paint.

In Vitro Diagnostics

In Vitro Assays: The microspheres described herein are useful as solid phase particles in an assay, such as an enzyme-linked immunosorbant assay, dot-blot, or Western blot, for the detection of a particular target such as a cell, biomolecule or drug in a biological sample. The microspheres designed for this use are composed of affinity molecules specific for the target molecule. For example, the macromolecule is an immunoglobulin, cell receptor or oligonucleotide probe and is bound to a test tube or microtiter plate.

For detection or quantitation of a target molecule of interest, a sample is combined with a solution containing the microspheres, the macromolecules on the microspheres are reacted with the target molecule, the microspheres are separated from any non-bound components of the sample, and microspheres containing bound molecules are detected by conventional methods. Fluorescently stained microspheres are particularly well suited for flow cytometry analysis in accordance with methods well known to those skilled in the art.

Histopathology: The microspheres described herein are useful as visual probes or markers of pathology in a histological sample. The macromolecules of microspheres designed for this use are specific for biomolecules expressed during a particular pathologic condition and are labeled with a detectable label. For example, the macromolecule is an immunoglobulin, cell receptor or oligonucleotide probe specific for an abnormal cell, such as a rapidly proliferating cell, or pathological organism, for example, a virus.

For detection of a pathogenic condition, a histological sample is combined with a solution containing the microspheres, the labeled macromolecules on the microspheres are reacted with the target molecule of interest, and bound microspheres are detected by detecting the label in accordance with methods well known to those skilled in the art.

In Vivo Diagnostics-Imaging

The microspheres described herein are useful as imaging agents for in vivo localization of a particular molecule, cell type or pathologic condition in a manner similar to that described above with regard to the use of the microspheres for histopathology. The macromolecules on microspheres designed for this use are specific for molecules expressed by a particular cell or pathologic organism and are labeled with a detectable label. For example, the macromolecule is an immunoglobulin, cell receptor or oligonucleotide probe specific for a tumor cell or pathological organism, such as a virus.

The microspheres are used to either detect a pathologic condition or to monitor the success of therapy, such as chemotherapy or surgery to ensure that the size of an abnormal tissue tumor has decreased or has been completely excised. For this use, a patient receives an administration of a microsphere solution, preferably intravenously, the labeled macromolecules on the microspheres are given a sufficient amount of time to localize to the affected organ or region of the body, the macromolecule is reacted with a target molecule expressed by the cell or organism under investigation, and bound microspheres are detected by detecting the label by conventional imaging techniques well known to those skilled in the art, such as x-ray.

Drug Delivery Systems

The microspheres are useful for therapy or prophylaxis when the macromolecule is a therapeutic agent or a pharmaceutical compound that is delivered to a patient and slowly released from the microspheres over time. These microspheres are particularly useful for slow release of drugs with short biological half-lives, such as proteins or peptides. If the pharmaceutical compound cannot be formed into a particle, then it is complexed to a carrier, such as albumin, and the carrier-pharmaceutical compound complex is formed into a microsphere. The microsphere can either provide for the slow release of the agent throughout the body or the microsphere can include an affinity molecule specific for a target tissue, or tumor, and be injected into a patient for targeted slow release of the therapeutic agent, such as an antitumor, antiviral, antibacterial, antiparasitic, or antiarthritic agent, cytokine, hormone, or insulin directly to the site requiring therapy. As discussed above, the affinity molecule may be cleavable.

Microspheres composed of antigenic proteins or polysaccharide-protein conjugates capable of provoking an immune response are particularly suitable for use as vaccines.

The microspheres are also useful as vehicles for gene therapy or the production of "genetic vaccines" when composed of nucleic acids, such as DNA or RNA, that are either incorporated into the DNA of the patient or are transfected into a target cell to produce a desired protein. For example, polynucleotides encoding core proteins of viruses such as influenza or human immunodeficiency virus HIV can be delivered as microspheres for expression of an antigenic protein. This is advantageous in that new vaccines need not be developed as often because viral core proteins mutate to a much lesser extent than the cell surface antigens currently used in vaccines. The nucleic acid microspheres are delivered to mammalian cells in much the same way as naked DNA is delivered. The desired nucleic acid sequence is inserted into a vector, such as plasmid DNA, with a promoter, such as the SV40 promoter or the cytomegalovirus promoter, and optionally may include a reporter gene, such as beta-galactosidase. The nucleic acid is preferably combined with a carrier protein and/or a cation, such as polylysine, to facilitate particle formation as described above. The microspheres are then administered directly to the patient or are transfected into mammalian cells that are then administered to the patient requiring therapy or prophylaxis. The nucleic acid microspheres may include a substance such as chloroquine, which allows nucleic acids to escape from cytoplasmic compartments into the cytoplasm so that it can be more easily transcribed and translated by the cells. Additionally, the microspheres may be coated with a substance that increases the efficiency of translation or may be coated with a substance to provide cell-specific targeting of the microspheres.

Research Applications

The microspheres are useful as research tools for the purification of a biomolecule from a complex mixture, as a reagent for the detection or quantification of a biomolecule, or for the production of biomolecules, such as antibodies.

For example, microspheres composed of a macromolecule, such as an immunoglobulin, are attached to a chromatography column and used in immunoaffinity chromatography to separate a ligand from a complex mixture. It will be understood by those skilled in the art that microsphere for use in high pressure liquid chromatography should be first attached to a non-compressible solid phase sphere or bead so that the column packing maintains its rigid structure under pressure.

Alternatively, microspheres including a labeled macromolecule or a mixture of labeled macromolecules specific for different cells or cell receptors are used to detect changes in the number of cells or cell surface receptors in response to a particular test condition using techniques such as flow cytometry.

The invention will be more fully understood by reference to the following examples. These examples, however, are merely intended to illustrate the embodiments of the invention and are not to be construed to limit the scope of the invention.

EXAMPLES

Example 1

Preparation of Microspheres Containing a Pharmaceutical Agent

Human serum albumin (HSA) Microspheres suitable for use as a drug delivery vehicle were prepared.

Preparation of Rifampicin TM-HSA Microspheres

Carbonyl diimidazole (124 mg, Sigma Chemical Co., St. Louis, Mo.) was added to a solution of 50 mg of the antibiotic Rifampicin TM (3-[4-methylpiperazinyliminomethyl] rifamycin, Sigma Chemical Co., St. Louis, Mo.) in 2 ml dimethylformamide (DMF). The resulting mixture was allowed to stand at room temperature for four hours. To the mixture was added a mixture of 1 ml of human serum albumin (HSA, 25%, Armour Pharmaceutical Co., Collegeville, Pa.) and 2 ml deionized water. The mixture was left at room temperature overnight. 14 ml of a polymer solution containing 25% PVP (40,000 daltons) and 25% PEG (3,350 daltons) in 0.in NaOAc, pH 4 was added to the mixture. The mixture was incubated for 30 minutes at room temperature, for 30 minutes at 37° C., and for 30 minutes at 58° C. and then cooled to room temperature. Particles were isolated by centrifugation, washed with deionized water three times and resuspended in 20 ml of water. The percentage of HSA incorporated into the particles was 74% (assayed by the BCA TM protein assay (Pierce, Rockford, Ill.)). The percentage of Rifampicin TM incorporated into the particles was greater than 6.8%. The average size of the particles was determined to be 68 nm in diameter using a Coulter TM cell sorter.

Preparation of Virazole TM-HSA Micro spheres

Carbonyl diimidazole (100 mg, Sigma Chemical Co., St. Louis, Mo.) was added to a solution of 36 mg of the antiviral drug Virazole Registered TM (ICN Pharmaceuticals, Inc., Costa Mesa, Calif.) in 0.2 ml of dimethylformamide (DMF). The resulting mixture was allowed to stand at room temperature for four hours. To the mixture was added a mixture of 0.2 ml of human serum albumin (HSA) (25%, Armour Pharmaceutical Co., Collegeville, Pa.) and 0.4 ml of deionized water. The mixture was incubated for 30 minutes at room temperature, for 30 minutes at 37° C., and for 30 minutes at 58° C. and then cooled to room temperature. Particles were isolated by centrifugation, washed with deionized water three times and resuspended in 20 ml of water. The percentage of HSA incorporated into the particles was 61% (assayed by the BCA TM protein assay (Pierce, Rockford, Ill.)). The percentage of Virazole Registered TM incorporated into the particles was 10%.

Example 2

Attachment of Polysaccharide to Outer Surface of Protein Microspheres

The polysaccharide PRP-AH was coupled to the outer surface of two different protein microspheres.

An adipic acid dihydrazide derivative (AH) of the polyribosylribitol phosphate (PRP) of Haemophilus influenza type b (Hib), one of the major causative organisms of bacterial meningitis, referred to as PRP-AH, was prepared by coupling PRP to adipic acid (Sigma Chemical Co., St. Louis, Mo.) in the presence of cyanogen bromide (Sigma Chemical Co., St. Louis, Mo.) (The PRP was obtained from the Massachusetts Public Health Biologic Laboratory (Jamaica Plain, Mass.)).

Coupling of PRP-AH to Ovalbumin Microspheres

Ovalbumin microspheres were prepared by adding ovalbumin (1%, Sigma Chemical Co., St. Louis, Mo.) to a polymer solution containing 25% PVP (40,000 daltons) and 25% PEG (3,500 daltons). The mixture was incubated for 30 minutes at room temperature, 30 minutes at 37°, and 30 minutes at 58° C., causing the formation of microspheres. The particles were collected by centrifugation. The average diameter of the particles was determined to be approximately 0.068 μm. The ovalbumin particles (1.5 mg) in 1M MES buffer, pH 5.0 (0.1 ml) were combined with the PRP-AH (1.5 mg). Subsequently, 2.79 mg of 1-ethyl-3-(3-dimethylaminopropyl-carbodiimide hydrochloride (EDC, Sigma Chemical Company, St. Louis, Mo.) were added. The reaction was mixed at room temperature for three hours. The particles were collected by centrifugation and washed three times with 1M MES buffer pH 5.0 (400 mu 1). The yield of PRP was determined to be 25% by the Anthrone free polysaccharide assay described in METHODS IN IMMUNOLOGY AND IMMUNOCHEMISTRY, Vol. 11, Williams, C. A. and Chase, M. W.(eds.), 1968, pp. 288–289, Academic Press, NY. Protein content was determined to be 55% by the BCA TM protein assay (Pierce, Rockford, Ill.). The ratio of PRP to protein was 0.46. The average diameter of the resulting particles was 0.067 um.

The recovery of free polysaccharide and the loading of polysaccharide on the particles (polysaccharide:ovalbumin ratio) was dependent on the starting ratio of polysaccharide to ovalbumin particle. As the ratio of polysaccharide to ovalbumin particle was increased, the recovery of free polysaccharide was decreased and the loading of polysaccharide onto the particles was increased as shown in Example Table 1 below.

EXAMPLE TABLE 1: Polysaccharide Recovery and Loading on Ovalbumin Microspheres

| Starting Ratio of Polysaccharide: Particle | Polysaccharide Recovery (%) | Loading of Polysaccharide |
|---|---|---|
| 1:1 | 25 | 0.46 |
| 1:2 | 30 | 0.29 |
| 1:4 | 66 | 0.21 |
| 1:8 | 94 | 0.14 |

Coupling of PRP-AH to Tetanus Toxoid Microspheres

Tetanus toxoid, (27 mg/ml, obtained from the Massachusetts Public Health Biologic Laboratory (Jamaica Plain, Mass.)) was combined with two volumes of a polymer solution containing 25% PVP (40,000 daltons) and 25% PEG (3,500 daltons), pH 5.0. The mixture was incubated for 30 minutes at room temperature, 30 minutes at 37o C., and 30 minutes at 58° C., causing the formation of microspheres. The particles were collected by centrifugation. The average diameter of the particles was determined to be approximately 0.082 um.

The tetanus toxoid particles (0.825 mg) in 1M MES buffer, pH 5.0 (0.1 ml) were combined with the PRP-AH (1.5 mg). Subsequently, 2.79 mg of 1-ethyl-3-(3-dimethylaminopropyl-carbodiimide hydrochloride (EDC, Sigma Chemical Company, St. Louis, Mo.) were added. The reaction was mixed at room temperature for three hours. The particles were collected by centrifugation and washed three times with 1M MES buffer pH 5.0 (400 mu 1). The yield of PRP was determined to be 16% by the Anthrone free polysaccharide assay described in METHODS IN IMMUNOLOGY AND IMMUNOCHEMISTRY, Vol. 11, Williams, C. A. and Chase, M. W.(eds.), 1968, pp. 288–289, Academic Press, NY. Protein content was determined to be 99% by the BCA TM protein assay (Pierce, Rockford, Ill.). The ratio of PRP to protein was 0.1. The average diameter of the resulting particles was 0.080 um.

Example 3

Release of Radiolabeled Protein and Polymer from Microspheres

Microspheres were prepared using Radiolabeled protein (bovine serum albumin, BSA) and Radiolabeled polymer (PEG). The release of radioactivity was measured as a function of time.

Microspheres were prepared by combining Radiolabeled protein (10 mg/ml [14] C.-BSA, NEN, Boston, Mass.) with two volumes of a polymer solution containing 25%PVP (40,000 daltons) and 25% [3] H-PEG (3,500 daltons, NEN, Boston, Mass.), pH 5.0. The mixture was incubated for 30 minutes at 37° C., 30 minutes at 58° C., and 30 minutes at 70° C. causing the formation of microspheres. The particles were collected by centrifugation.

Figure 1:
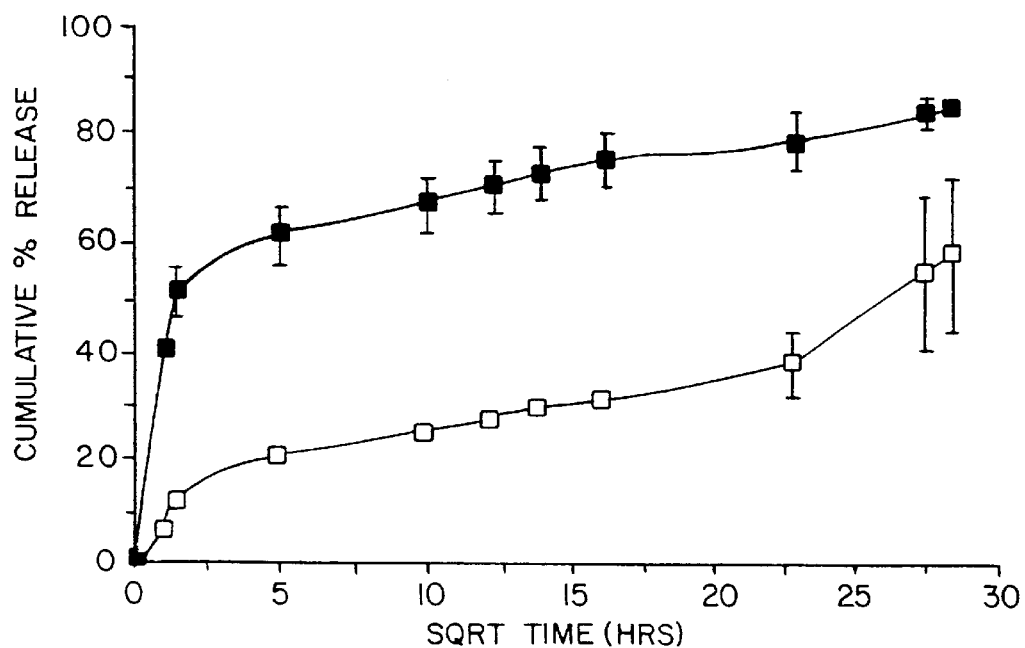
FIG. 1 is a graph showing the cumulative percent of radiolabeled polyethylene glycol (PEG) and radiolabeled bovine serum albumin (BSA) released from microspheres versus the square root of time in hours. The black square symbol represents PEG, and the open square symbol represents BSA.

Protein and polymer were slowly released from the microspheres by adding 500 ml of phosphate buffered saline (pH 7.4) and incubating the mixture at 37° C., while shaking mildly using a Nutator TM rotator. At various time points, particles were precipitated by centrifugation at 8,000 rpm for 10 minutes, the supernatant was removed with a pipette, and radioactivity was assayed by adding liquid scintillation fluid and counting in a liquid scintillation counter. The particles were then resuspended in 500 ml of phosphate buffered saline (pH 7.4) and replaced at 37° C. with gentle rotation until the next time point. The release kinetics of Radiolabeled protein and polymer during incubation at 37° C. is shown in FIG. 1.

Figure 2:
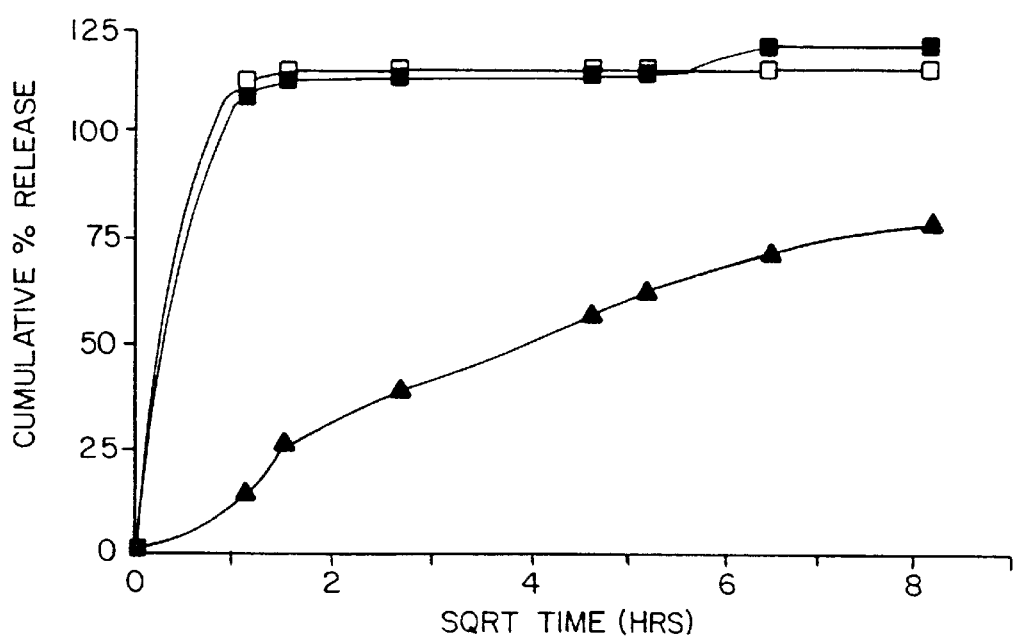
FIG. 2 is a graph showing the cumulative percent of radiolabeled bovine serum albumin (BSA) released from microspheres prepared with three different concentrations of polymer versus the square root of time in hours. The gray square symbol represents a total polymer concentration of 50%, the open square symbol represents a total polymer concentration of 40%, and the black triangle symbol represents a total polymer concentration of 25%.
Figure 3:
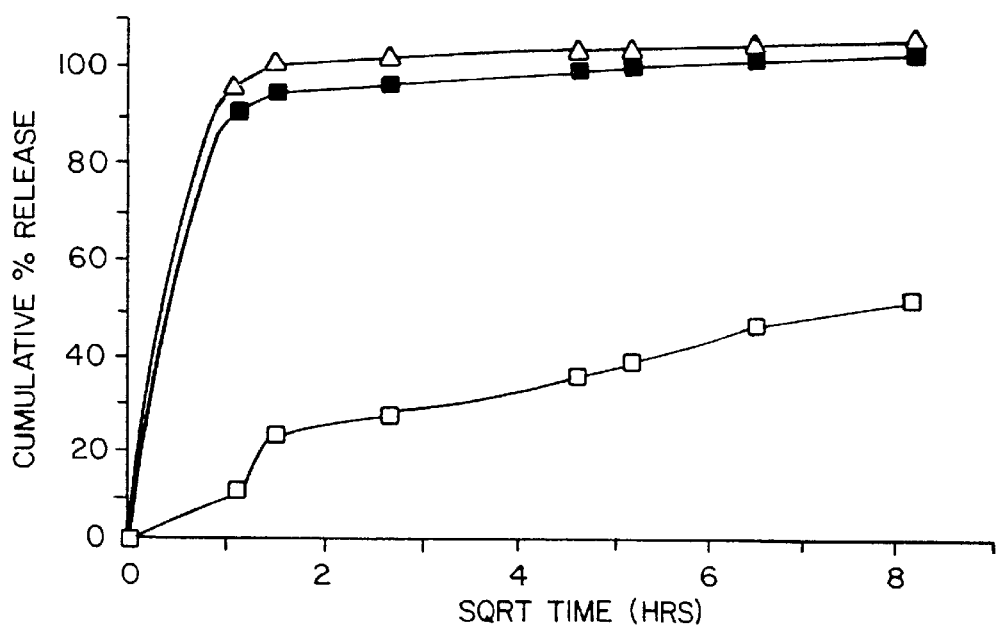
FIG. 3 is a graph showing the cumulative percent of radiolabeled polyethylene glycol (PEG) released from microspheres prepared with three different concentrations of polymer versus the square root of time in hours. The open triangle symbol represents a total polymer concentration of 50%, the black square symbol represents a total polymer concentration of 40%, and the open square symbol represents a total polymer concentration of 25%.

Microspheres were prepared and assayed for release as described above, however, three different concentrations of polymer were used, and the microspheres were formed by incubation at 58° C. In the first preparation, 25% PEG and 25% PVP were used. In the second preparation, 20% PEG and 20% PVP were used. In the third preparation, 12.5% PEG and 12.5% PVP were used. The release kinetics of Radiolabeled protein is shown in FIG. 2. The release kinetics of Radiolabeled polymer is shown in FIG. 3.

Figure 4:
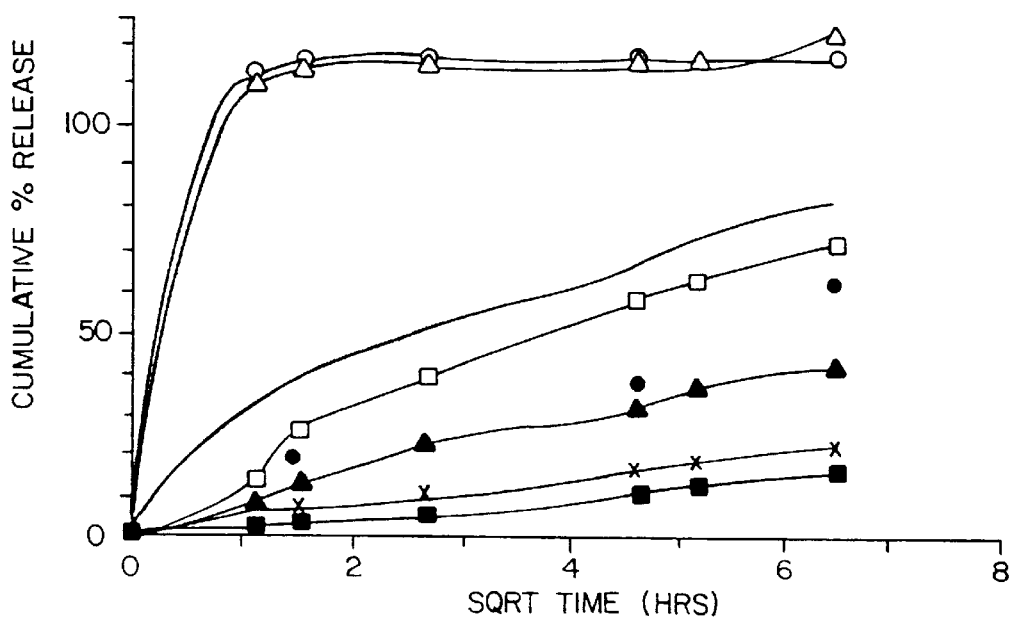
FIG. 4 is a graph showing the cumulative percent of radiolabeled bovine serum albumin (BSA) released from microspheres prepared with three different concentrations of polymer at various incubation temperatures versus the square root of time in hours. The open square symbol represents a total polymer concentration of 25% and incubation at 58° C., the black square symbol represents a total polymer concentration of 25% and incubation at 70° C., the open circle symbol represents a total polymer concentration of 40% and incubation at 58° C., the black circle symbol represents a total polymer concentration of 40% and incubation at 70° C., the open triangle symbol represents a total polymer concentration of 50% and incubation at 58° C., the black triangle symbol represents a total polymer concentration of 50% and incubation at 70° C., the light "X" symbol represents a total polymer concentration of 25% and incubation at 37° C. and 58° C., and the dark "X" symbol represents a total polymer concentration of 25% and incubation at 37° C. and 70° C.
Figure 5:
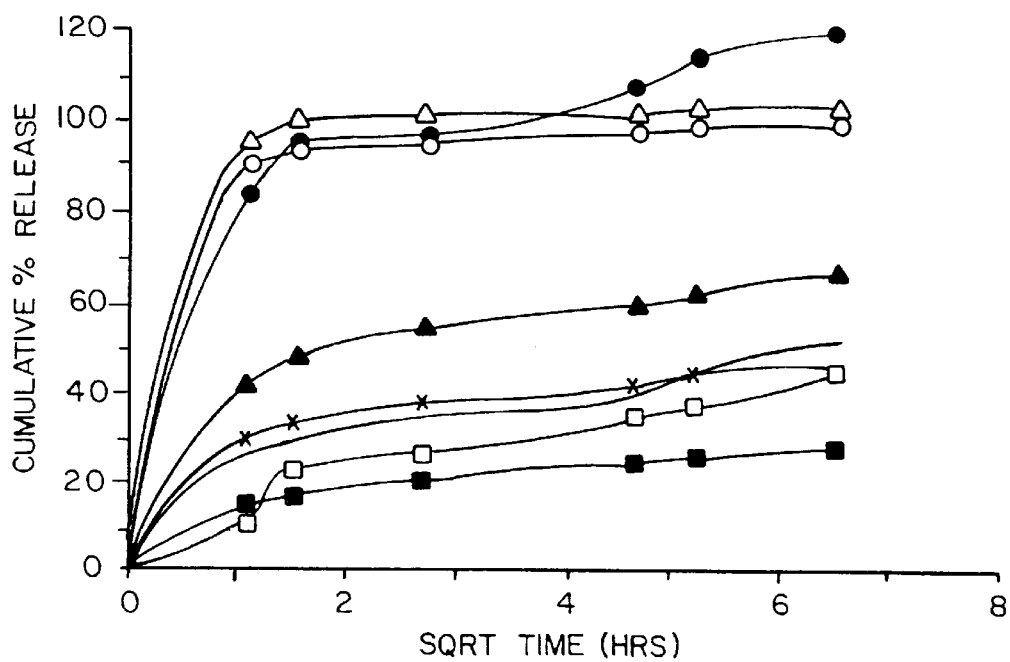
FIG. 5 is a graph showing the cumulative percent of radiolabeled polyethylene glycol (PEG) released from microspheres prepared with three different concentrations of polymer at various incubation temperatures versus the square root of time in hours. The symbols are the same as those described in FIG. 4.
Figure 6:
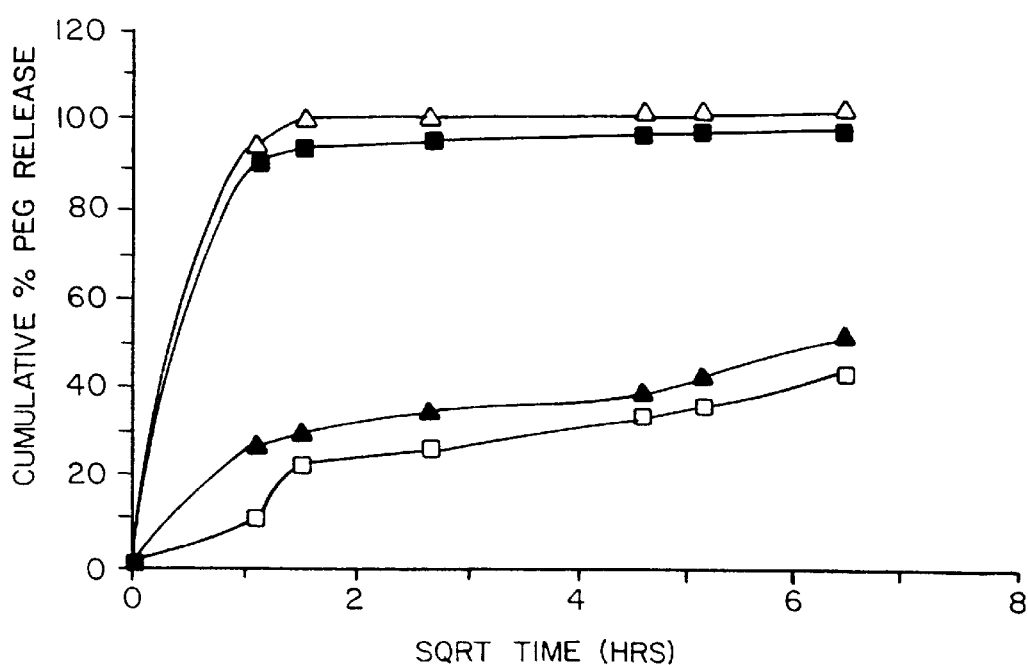
FIG. 6 is a graph showing the cumulative percent of radiolabeled polyethylene glycol (PEG) released from microspheres prepared with three different concentrations of polymer at an incubation temperature including 58° C. versus the square root of time in hours. The open triangle symbol represents a total polymer concentration of 50% and incubation at 58° C., the black square symbol represents a total polymer concentration of 40% and incubation at 58° C., the gray triangle symbol represents a total polymer concentration of 25% and incubation at 37° C. and 58° C., and the open square symbol represents a total polymer concentration of 25% and incubation at 58° C.

Microspheres were once again prepared and assayed for release as described above, however, three different concentrations of polymer were used, and the microspheres were formed by incubation at 58° C., 70° C., both 37° C. and 58° C., and both 37° C. and 70° C. The release kinetics of Radiolabeled protein is shown in FIG. 4. The release kinetics of Radiolabeled polymer is shown in FIG. 5. Radiolabeled PEG release as a function of polymer concentration is shown in FIG. 6.

Example 4

Formation of DNA-Containing Microspheres

DNA-containing microspheres were prepared and transfected into fibroblast cells. The microspheres were analyzed for transfection efficiency and protein expression.

A 0.025 mL aliquot of a 1 mg/mL solution of a plasmid DNA (pCMV beta Gal, Promega, Milwaukee, Wis.) was complexed with 0.025 mL of a 5.0 mg/mL solution of poly-L-lysine having an average molecular weight range of from 1 kDa to 40 kDa (Sigma Chemical Co., St. Louis, Mo.).

To the plasmid DNA-poly-L-lysine complex was added, while vortexing, 0.1 mL of a solution of 25% (weight/volume) polyvinylpyrrolidone (average molecular weight 40 kDa, Spectrum, Gardena, Calif.) and 25% (weight/volume) polyethylene glycol (average molecular weight 3.35 kDa, Spectrum, Gardena, Calif.) in O.1M sodium acetate, pH 5.5.

The mixture was incubated at 37° C. for 30 minutes and then at 70° C. for 30 minutes. DNA-containing microspheres were formed. The mixture was centrifuged at 17,500×g for 10 minutes, the supernatant aspirated, and the particles washed three times with 0.3 mL of 10% glycerol (volume/volume) in deionized water. The microspheres were resuspended in 0.050 mL deionized water. The DNA-containing microspheres were applied to NIH3T3 fibroblast cells and incubated up to 24 hours to allow microsphere uptake by the cells. Uptake was terminated by washing the cells three times with phosphate buffered saline (PBS/Ca[2+]+Mg[2+]-free) (GIBCO-BRL, Gaithersburg, Md.) and the addition of Dulbecco's Minimal Essential Media (DMEM, GIBCO-BRL, Gaithersburg, Md.).

Figure 7:
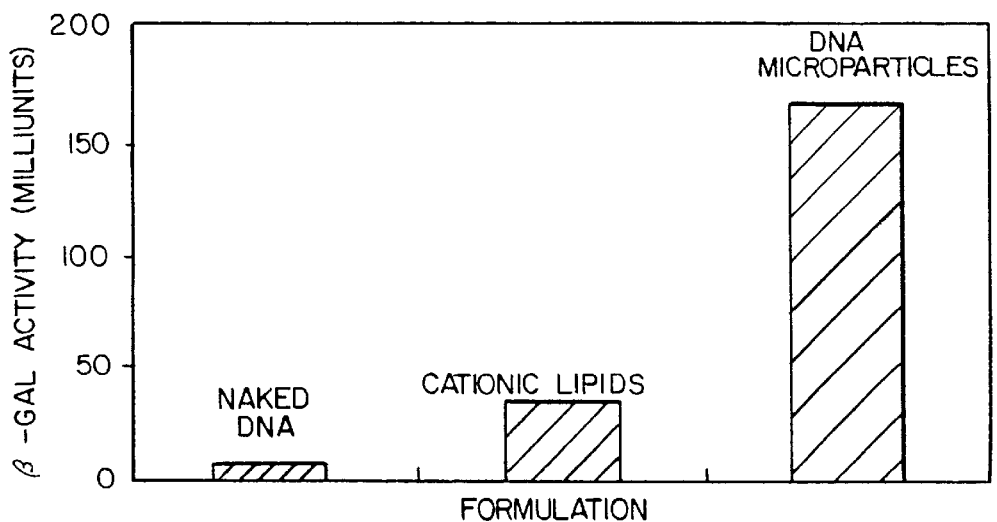
FIG. 7 is a bar graph showing the amount of expressed gene product by beta -galactosidase activity in milliunits versus microsphere formation for naked DNA, cationic liposomes containing DNA, and DNA microspheres.

The uptake and expression of the pCMV beta Gal DNA was assayed for efficiency of transfection and amount of expressed beta -galactosidase enzyme. The efficiency of transfection was determined by fixation of the cells and color development with the beta-galactosidase enzyme substrate X-Gal (5-bromo-4-chloro-3-indolyl-beta-D-galactopyranoside, GIBCO-BRL, Gaithersburg, Md.). The amount of expressed beta-galactosidase enzyme was determined by lysing the transfected cells and measuring total enzyme activity with the beta -galactosidase enzyme substrate CPRG (chlorphenolred-beta-D-galactopyranoside, Boehringer Mannheim, Indianapolis, Ind.) Results: The amount of expressed beta-galactosidase enzyme from lysed cells that were transfected using either: 1) naked DNA (no addition); 2) cationic liposomes plus DNA; or 3) DNA-containing microsphere, prepared as described above, is shown in FIG. 7.

Example 5

Formation of Leuprolide Acetate-Containing Microspheres

Microspheres containing leuprolide acetate peptide and human serum albumin were prepared. Leuprolide acetate is a generic analog of luteinizing hormone releasing hormone, which is a peptide used primarily in the treatment of prostate cancer.

A 0.010 mL aliquot of a solution of 10–100 mg/mL leuprolide acetate in water (LHRH, TAP Pharmaceuticals, Deerfield, Ill.) was added to 0.168 mL of a 2–10% (weight/volume) solution of dextran sulfate in water (average molecular weight 500 kDa), and the solution was thoroughly mixed. To the leuprolide/dextran solution was added a 0.856 niL aliquot of a solution containing 25% (weight/volume) polyethylene glycol, having an average molecular weight of 3.35 kDa (Spectrum, Gardena, Calif.), and 25% (weight/volume) polyvinylpyrrolidone, having an average molecular weight of 40 kDa, in an aqueous solution of 0.1M sodium acetate, pH 5.5. The resulting solution was thoroughly mixed and allowed to stand for up to 30 minutes. A 0.25 mL aliquot of a 20% (weight/volume) solution of human serum albumin (Sigma Chemical Co., St. Louis, Mo.) in water was then added to the solution. The final solution was thoroughly mixed and placed in a water bath at between 70° C. and 90° C. for a period of time between 30 minutes and 3 hours. Microspheres were formed.

The microspheres were collected by centrifugation at 17.5K×g for 10 minutes, washed in 0.5 mL of dH2O, and collected again by centrifugation.

Sterile particles were prepared using the foregoing procedure and by sterile filtering all solutions prior to use and conduction all open tube manipulations in a laminar flow tissue culture hood.

Figure 8:
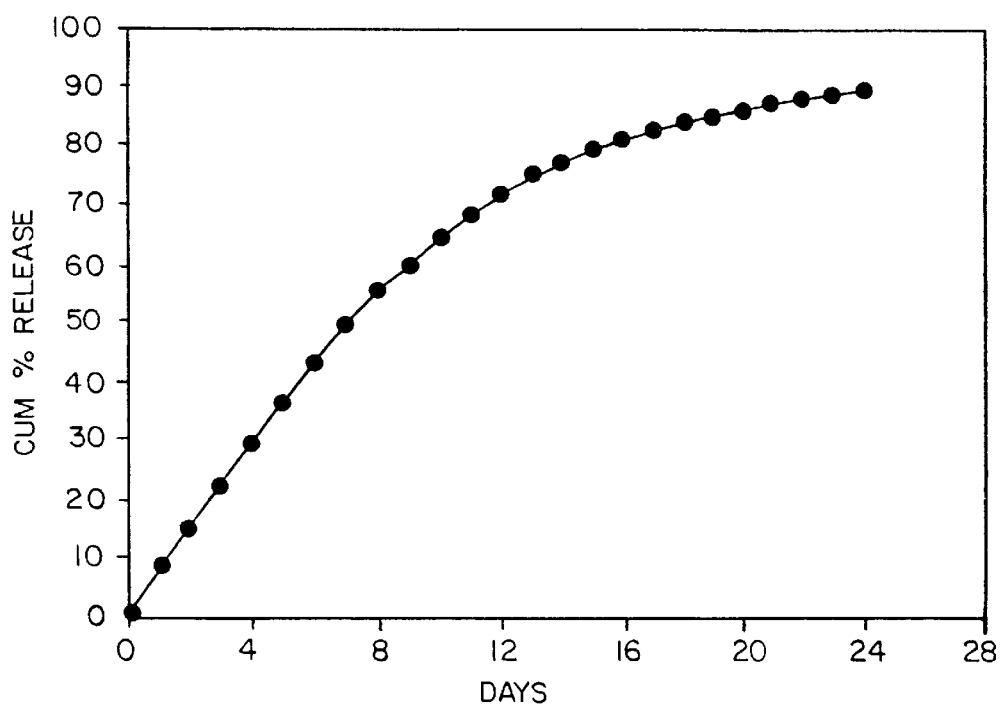
FIG. 8 is a graph of cumulative percent release of leuprolide acetate from microspheres over time in days.

In vitro release of leuprolide acetate was measured by centrifugation of microspheres and resuspension in a phosphate buffered saline release medium. The release kinetics are shown in FIG. 8.

The microspheres were composed of approximately 10% leuprolide acetate, 50% human serum albumin, 20% dextran sulfate and 20% polyethylene glycol/polyvinylpyrrolidone.

Similar particles were prepared which also included zinc sulfate or caprylic acid, both of which retarded the release of protein and peptide from the microspheres.

Example 6

Preparation of Bovine Serum Albumin Microspheres Using Polyethylene Glycol and Poloxamer 407

Bovine serum albumin microspheres were prepared using a polymer mixture of polyethylene glycol and poloxamer 407. 1.25 grams of polyethylene glycol (MW 3550, Sigma Chemical Co., St. Louis, Mo.) and poloxamer 407 (BASF, Parsippany, N.J.) were dissolved in 100 ml of a 0.1N sodium acetate buffer, pH 5.5 to make a 12.5% solution. A solution of 10 mg/ml bovine serum albumin (BSA, Fraction V, Sigma Chemical Co.) was dissolved in dH2O. A 400 ml aliquot of the BSA solution was combined with 800 ml of the polymer solution. The mixture was vortexed. A clear solution formed. The solution was heated to 70° C. for 30 minutes. Particle formation was observed by the presence of a milky white suspension.

The residual polymer solution was removed by centrifugation at 12,500 rpm for 10 minutes and then decanting the solvent. Two washes and centrifugation steps with 10% ethanol in water were performed to remove additional residual polymer.

Example 7

Preparation of Bovine Serum Albumin Microspheres Using Dextran

Bovine serum albumin microspheres were prepared using dextran. 12.5 grams of dextran (MW 500,000, Sigma Chemical Co., St. Louis, Mo.) were dissolved in 100 ml of a 0.1M sodium acetate buffer, pH 5.0 to make a 12.5% solution. Bovine serum albumin (BSA, Sigma Chemical Co.) was dissolved in dH20 at a concentration of 10 mg/ml. A 400 ml aliquot of the BSA solution was place in a 1.5 ml microcentrifuge tube. An 800 ml aliquot of the dextran polymer solution was added to the BSA solution. The solution was vortexed. A clear solution formed. The microcentrifuge tube was place in a 70° C. water bath for 30 minutes. A milky white suspension was observed, indicating microsphere formation.

Residual dextran polymer solution was removed by centrifugation at 12,500 rpm for 10 minutes and then decanting the solvent. Two washes and centrifugation steps with 10% ethanol in water were performed to remove additional residual polymer. Scanning electron micrographs revealed the formation of sub-micron sized microspheres often arranged in a string-like structure.

Example 8

Preparation of Bovine Serum Albumin Microspheres Using Eudragit Registered TM E100

Bovine serum albumin microspheres were prepared using Eudragit® E100 polymer. This polymer is soluble in an organic solvent that is miscible with water.

Eudragit® E100 polymer (Rohm, Malden, Mass.) was dissolved in a 1:1 solution of 0.1M sodium acetate buffer (pH 5.0) and ethanol. The final pH of the solution was pH 6.5. A 400 ml aliquot of a 10 mg/ml solution of bovine serum albumin (BSA, Sigma Chemical Co., St. Louis, Mo.) was combined with 800 ml of the Eudragit® E100 polymer solution. A clear solution formed. The BSA/polymer solution was incubated in a 70° C. water bath for 30 minutes. A milky white suspension was observed, indicating microsphere formation. The particles were collected by centrifugation for 10 minutes at 8,000 rpm and decantation of the liquid.

Example 9

Preparation of Insulin Microspheres Using Dextran

Insulin microspheres were prepared using dextran polymer.

A 20% (weight/weight) solution of dextran polymer (MW 500,000, Sigma Chemical Co., St. Louis, Mo.) was dissolved in pH 5.0 sodium acetate buffer. 1.9 ml of dH20 was added to 20.5 mg of insulin (Sigma Chemical Co.). 100 ml of 0.2M HCL was added to dissolve the insulin. A 400 ml aliquot of the insulin solution was placed in a test tube. An 800 ml aliquot of the dextran solution was added to the insulin solution. The mixture was vortexed. The mixture turned cloudy upon addition of the dextran solution. The tubes were heated to a final temperature of either 70° C. or 90° C. to form insulin microspheres. The microspheres were centrifuged at 10,000 rpm for 5 minutes and the liquid decanted to remove residual polymer. The microspheres were washed with 10% ethanol in water.

The microspheres were place in a phosphate buffered saline solution, pH 7.4 to determine the dissolution characteristics. The insulin particles formed at a final temperature of 90° C. did not dissolve in the phosphate buffered saline whereas the insulin particles prepared at a final temperature of 70° C. dissolved within 15 minutes. Therefore, insulin particle stability may be adjusted by varying the incubation temperature employed during particle formation.

Example 10

Preparation of Microspheres Using Various Polymers

Human serum albumin microspheres were prepared using nine different polymers or mixtures of polymers.

Procedure: A protein solution (1–5% human serum albumin, pH 4.5–5.5 or bovine serum albumin) in a buffer was prepared. The following polymer solutions were prepared:

polyethylene glycol/polyvinylpyrrolidone (3 kDa PEG/40 kDa PEG in a 1:1 mixture); hetastarch (500 kDa); Pluronic L-101™ polymer; dextran (3–500 kDa); dextran sulfate (3–500 kDa); polyvinylpyrrolidone (10–360 kDa); polyethylene glycol/polyvinylpyrrolidone with inulin (a polysaccharide); polyethylene glycol/polyvinylpyrrolidone with Pluronic L-101™ polymer; dextran with Pluronic L-101™ polymer. Approximately one volume of protein solution was mixed with two volumes of polymer solution. The mixture was incubated in a water bath at 70° C. to 90° C. for thirty minutes. The mixture was then placed in an ice bath. Microsphere formation was observed.

The microspheres were centrifuged until compacted into a pellet, the supernatant decanted, and the pellet washed twice in a 10% ethanol in water solution to remove the residual polymer solution. Microspheres were then washed three times with deionized water. The microspheres were used or tested immediately or were lyophilized for subsequent use.

Observations: Microspheres prepared using polymers having a higher molecular weight or a higher concentration of polymers provide a more viscous medium which produced a more uniform microsphere size distribution. The inclusion of a surfactant, such as Pluronic L-101™ polymer or mixing during microsphere formation affected microsphere size. An increase in protein concentration during microsphere formation caused an increase in the incorporation of protein into the microspheres. An increase in polymer size generally caused an increase in protein incorporation into the microspheres. The use of different polymers affected release kinetics. For example bovine serum albumin (BSA) microspheres prepared using dextran released approximately 15% less BSA than microspheres prepared using PEG/PVP. However, the release of polysaccharide from protein-polysaccharide microspheres, such as the release of [3] H-inulin from human serum albumin/inulin microspheres, was more rapid when dextran rather than PEG/PVP was employed.

Example 11

Preparation of Protein Microspheres Containing Nafarelin Acetate Using Various Polymers Protein microspheres containing the drug nafarelin acetate were prepared.

Nafarelin acetate is useful in the treatment of endometriosis, precocious puberty and prostate cancer.

Procedure: Human serum albumin microspheres were prepared as described above in Example 10 using nine different polymers or mixtures of polymers. Nafarelin acetate (Roche Laboratories, Nutley, N.J.) was dissolved in deionized water to produce a 10 mg/ml solution.

To 1 mg of nafarelin acetate was added 10 mg of the human serum albumin microspheres. The mixture was vortexed and mixed for 16 hours at 4° C. A 3M ammonium sulfate solution was added to the mixture to a final concentration of 0.5M and vortexed and mixed for 15 minutes at ambient temperature. A 1M zinc sulfate solution was added to a final concentration of either 0.01M, 0. 1M or 1M and vortexed and mixed for 1 hour at ambient temperature.

The mixtures were centrifuged, supernatant decanted and pellet resuspended in deionized water three times to wash the microspheres.

Figure 9:
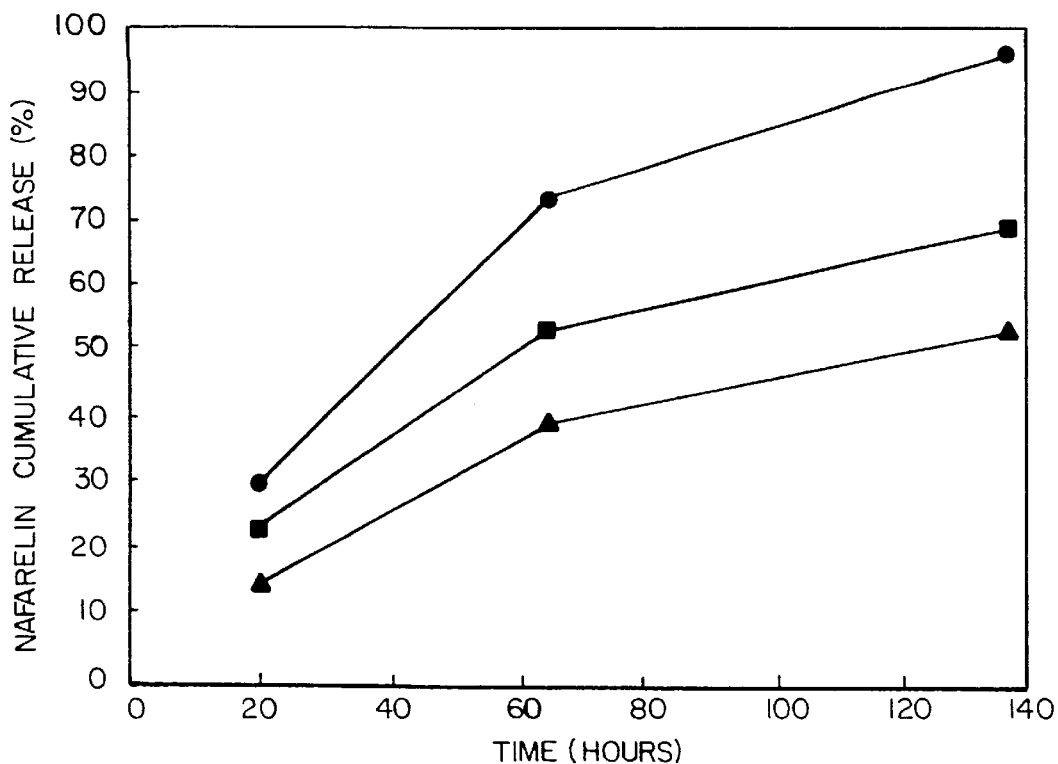
FIG. 9 is a graph of cumulative percent nafarelin acetate release versus time in hours for three concentrations of zinc sulfate used during microsphere preparation. The circle symbol represents 0.01M zinc sulfate; the square symbol represents 0. 1M zinc sulfate; and the triangle symbol represents 1M zinc sulfate.

Observations: The addition of zinc sulfate reduced the rate of release of nafarelin acetate from human serum albumin microspheres. The results are shown in FIG. 9.

Example 12

Preparation of Doxorubicin/Albumin Microspheres

Human serum albumin microspheres containing the chemotherapeutic drug doxorubicin were prepared.

To 1 mL of a solution of 250 mg/mL human serum albumin (Sigma, St. Louis, Mo.) in dH20 was added 0.05 mL of a 5 mg/mL solution of doxorubicin (Sigma Chemical Co., St. Louis, Mo.) in dH2O, the combined solution was mixed and allowed to stand at room temperature for 30 minutes. To the above solution was added 3.0 mL of a solution of 200 mg/mL dextran sulfate (MW 500,000, Sigma Chemical Co., St. Louis, Mo.) in dH2O, and the resulting solution was mixed and incubated at 37° C. for 30 minutes. The solution was then incubated at 70° C. for 30 minutes, after which 1.0 mL of 3.0M sodium acetate, pH 5.0, was added and the resulting solution mixed. The solution was then incubated at 90° C. for 30 minutes. Microspheres were formed. The microspheres were washed two times with 5.0 mL dH2O.

Example 13

Incorporation of LHRH into Dextran Sulfate/Albumin Microspheres

Luteinizing hormone releasing hormone was incorporated into microspheres composed of human serum albumin and dextran sulfate microspheres.

To 0.168 niL of a 10% (weight/volume) solution of dextran sulfate (average MW 500,000, Sigma Chemical Co., St. Louis, Mo.) in dH20 was added 0.25 mL of a 20% (weight/volume) solution of human serum albumin (Sigma Chemical Company, St. Louis, Mo.) in dH2O. The solution was thoroughly mixed, and 0.856 mL of a solution of 25% (weight/volume) polyethylene glycol (average MW 3.35 kDa, Spectrum, Gardena, Calif.) and 25% (weight/volume) polyvinylpyrrolidone (average MW 40 kDa, Spectrum, Gardena, Calif.) in an aqueous solution of 0.1M sodium acetate, pH 5.5 was added.

The resulting solution was thoroughly mixed and placed in a water bath at a temperature between 70° C. and 90° C. for between 30 minutes and 3 hours. Microspheres were formed. Microspheres were collected by centrifugation at 17.5K×g for 10 minutes, resuspended for washing in 0.5 mL of dH2O, and collected again by centrifugation. The microspheres were resuspended in 0.3 mL of a solution of 0.1M sodium acetate, pH 5.5. A 0.01 mL aliquot of a 10 mg/mL solution of luteinizing hormone releasing hormone (LHRH, Sigma Chemical Co., St. Louis, Mo.) in dH20 was added and incubated for 16 hours at room temperature to allow the LHRH peptide to bind to the microspheres. After the 16 hour binding incubation, the unbound LHRH peptide was removed by two cycles of washes with dH20 and collection by centrifugation. The yield of LHRH incorporation was typically 83 to 90%.

Example 14

Incorporation of Estradiol Into ProMaxx® Microspheres.

Human serum albumin microspheres were formed by combining 12.5 wt % polyethylene glycol and 12.5 wt % polyvinyl pyrollidone in 50 mM sodium acetate buffer at pH 5.3 and with 1% (wt/vol) human serum albumin dissolved in aqueous solution. The solution was placed at 70° C. for 30 minutes. The microspheres were formed and precipitated from solution. The microsphere suspension was washed 3 times in deionized water. Estradiol was then loaded into human serum albumin microspheres at 3 different weight percent loadings. The estradiol was dissolved in ethyl alcohol and incubated in the presence of the albumin microspheres. The affinity of estradiol for albumin by means of hydrophobic interactions resulted in the ability to load estradiol at various weight percent loadings. The 10% by weight estradiol containing microspheres contained 1 mg of estradiol and 8.33 mg of Human Serum Albumin (HSA). The 49% by weight estradiol containing microspheres contained 8.15 mg of estradiol and 8.33 mg of HSA. The 77% by weight estradiol containing microspheres contained 27.68 mg of estradiol and 8.33 mg of HSA The microspheres were released into phosphate buffered saline (PBS) at pH 7.4.

All samples were rotated at 20 rpm at 37° C. to insure constant mixing. One (1) mL of PBS was added to the microspheres which were housed in standard polypropylene centrifuge tubes. At each time point, the tubes were centrifuged, the supernatant removed, and the 1 mL of release media was placed in a sample vial. Each 1 mL sample was speed vacuum dried and resuspended in 200 µL of ethanol. The released estradiol was measured by HPLC.

Figure 10:
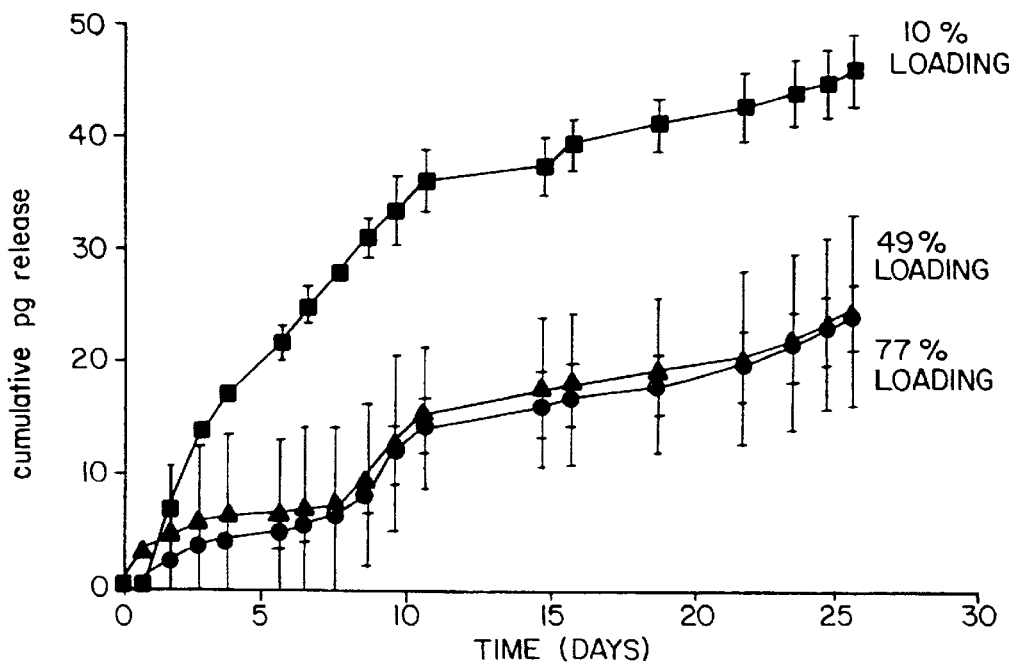
FIG. 10 shows the sustained release of estradiol in vitro from the microspheres of the invention.

The sustained release of estradiol in shown in FIG. 10.

Figure 11:
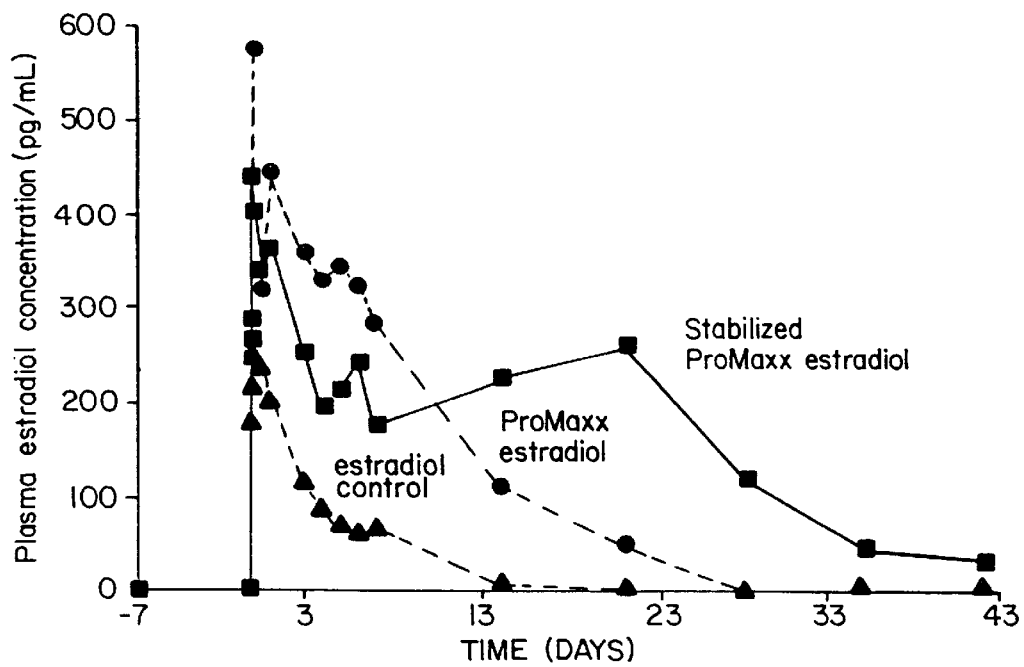
FIG. 11 shows the sustained release of estradiol in vivo (serum concentrations) from the microspheres of the invention.

The sustained release of estradiol was also demonstrated in vivo. The microspheres were injected into five dogs and the resulting serum concentrations were determined by radioimmuno assay for estradiol. The results are shown in FIG. 11. The three groups consisting of five dogs each included an estradiol control which resulted in the lowest concentrations and the shortest half life in vivo. ProMaxx® which are the albumin microspheres loaded with estradiol yielded substantially greater plasma estradiol concentrations with a significantly longer half life. And when the estradiol-microspheres were chemically stabilized with EDC (Ethyl dimethyl amino propyl carbodiimide), greater sustained plasma levels and increased half life of estradiol was observed over a 43 day period.

Example 15

Incorporation of Diclofenac Na Into ProMaxx® Microspheres.

Bovine serum albumin microspheres were formed by combining 12.5 wt % polyethylene glycol and 12.5 wt % polyvinyl pyrollidone in 50 mM sodium acetate buffer at pH 5.3 and with bovine serum albumin dissolved in aqueous solution. The solution was placed at 70° C. for 30 minutes. The microspheres formed and precipitated from solution. The microsphere suspension was washed 3 times in deionized water.

Figure 12:
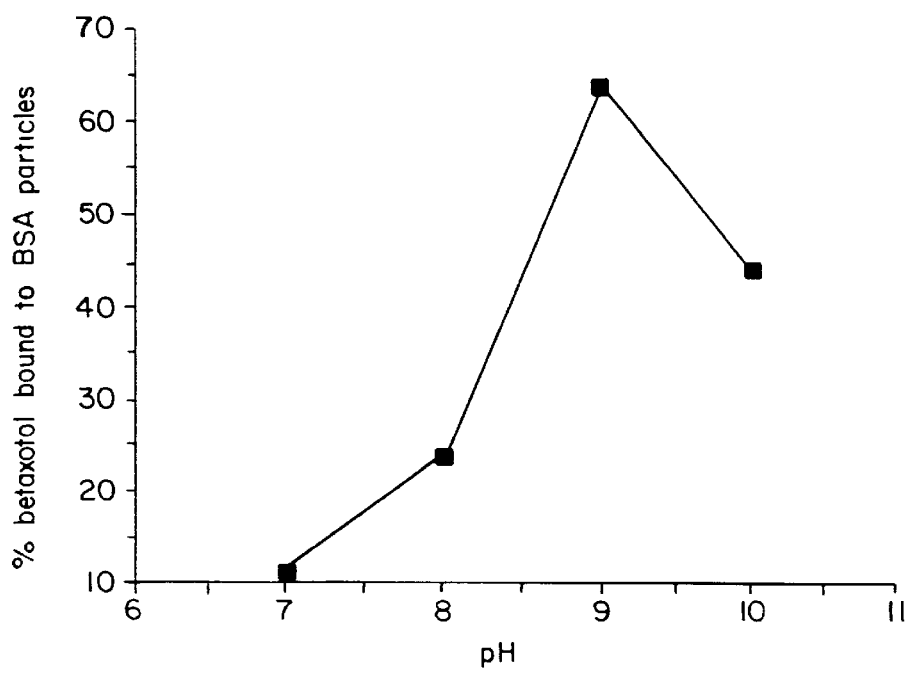
FIG. 12 shows the efficiency of diclofenac Na incorporation by adjusting the incubation conditions.

The non steroidal anti inflammatory drug diclofenac Na was bound to albumin microspheres by manipulating the degree of ionization of diclofenac Na by altering the pH of the incubating solutions. The efficiency of diclofenac Na incorporation could be optimized to 65% incorporation by adjusting the incubating conditions to a pH of as shown in FIG. 12.

Example 16

Formation of Leuprolide Acetate-Containing Microspheres

Leuprolide acetate is an analog of luteinizing hormone releasing hormone.

An aqueous solution of albumin (e.g., human, bovine, mouse, or rat serum albumin) is added to an aqueous solution of anionic complexing agent (dextran sulfate of molecular weight (MW) 10 kDa to 500 kDa or heparin or heparan sulfate or polyglutamic or polyaspartic acids) with or without an aqueous solution of divalent cations (calcium or magnesium or zinc) at ambient temperature and the resulting mixture is agitated for a period of time from 5 minutes to 3 hours. To this mixture is then added an aqueous solution of polymer (either polyethylene glycol (PEG) of MW 3.5 to 40 kDa; polyvinylpyrrolidone (PVP) of MW 6 to 40 kDa, or mixtures of both PEG and PVP, or starch or hydroxyethylstarch of MW 500 kDa). The concentration of albumin in the final mixture is from 5–30 g/L, of ionic complexing agent is from 5–30 g/L, of divalent cations from 0–30 g/L, and polymer concentration is from 100 g/L to 400 g/L. The mixture is agitated for a period from 5 minutes to 6 hours at ambient temperature. The temperature of the mixture is then raised to a temperature between 37° C. and 50° C. over a period of from 5 minutes to 3 hours. The microspheres are subjected to stabilization by the addition of a chemical stabilizer (EDC, or other linking agent) or by thermal stabilization by heating to a temperature of between 70° C. and 100° C. over a period of 0.5 to 6 hours. The mixture is subjected to stabilizer for a period of from 10 minutes to 16 hours or for thermal stabilization the temperature is maintained at the final value from 10 minutes to 6 hours. The microspheres are then collected and separated from the unincorporated components of the reaction mixture by filtration or centrifugation with subsequent washing or by diafiltration. Incorporation of leuprolide acetate to the microspheres is effected by adding an aqueous solution of leuprolide solution to an aqueous suspension of microspheres. The concentrations of microspheres are 1–50 g/L of leuprolide acetate are 1–100 g/L in an aqueous medium of from 0–100 mM buffer at pH between 2.5 and 10.0. After incubation of the leuprolide acetate with the microsphere suspension for 5 minutes to 8 hours at 5–50° C., peptide-containing microspheres are washed by the methods described above to remove unbound peptide. The peptide-containing microspheres are in some cases subjected to further stabilization by a repeat exposure to chemical stabilizers as described above, and then washed to remove unbound peptide. The final peptide-containing microspheres are then either resuspended in water or lypophylized. Their pharmaceutic efficacy is determined using a pharmacodynamic rat model of testosterone suppression over periods from 7 to 180 days. Leuprolide acetate-containing microspheres fabricated according to the above method have been injected into rats and leuprolide acetate has been detected in serum for from 7 to 120 days. Rat serum testosterone has been suppressed in rats so injected with the leuprolide acetate-containing microspheres for from 7 to 120 days. These results evidence the sustained release of physiologically active leuprolide acetate over this time period.

Example 17

Examples of Calcium-Containing ProMaxx Microspheres

The following example illustrates specific conditions for forming preferred microspheres of the invention. It is to be understood that the concentrations, times, and pH's can vary within a reasonable experimental amount and still result in microspheres having the characteristics described below. As described in the detailed description of the invention, it is preferred that the divalent metal (preferably calcium or magnesium) be added during the formation process and that such addition of the metal occur within 30 minutes of the addition of the other components which are used for formation of the microspheres. Further details regarding the microsphere formation procedure are provided below.

To 1 volume of a 25% (w/v) solution of dextran sulfate (avg MW 500 kDa) is added approximately 2 volumes of a 25% (w/v) solution of albumin (human) and the mixture is stirred thoroughly for at least 5 min. To this mixture approximately 6 volumes of a 36% (weight/volume) solution of hetastarch in aqueous 63 mM Na acetate is stirred thoroughly and to this hetastarch solution is added water while continuing thorough stirring. The resulting solution is stirred thoroughly for at least 5 min. whereupon the dextran sulfate-albumin mixture is added slowly to it. To this mixture a suitable volume of a 1.5 M solution of $CaCl_2$, $ZnCl_2$, or $MgCl_2$ is added to make a final mixture containing 25 mM or 100 mM metal cation. This mixture is constantly thoroughly stirred. The temperature of the reaction mixture is then increased to a final temperature of 60–90° C. over a period of 50–60 min. The temperature of the mixture is maintained at 60–90° C. for 30–120 min., whereupon an equal volume of a room temperature 25 mM solution of MES-$Na^+$ (N-morpholinoethanesulfonic acid) at pH 6.0±0.5 is added while stirring is continued. The formed microspheres are then diafiltered against 1 vol. Of 25 mM MES pH 6.0±0.5. The microspheres are then concentrated and diafiltered against 9 volumes of 25 mM MES pH 6.0±0.5 at room temperature. The loading and diafiltration are carried out at pH 4.5±0.5 in the case of $Zn^{2+}$-containing microspheres. The microspheres are concentrated by diafiltration. To the microsphere suspension containing 17.1 g of albumin (human) is added a solution of 3.43 g leuprolide acetate in 25 mM MES pH 6.0 at a rate of 0.4 liters per min. The leuprolide solution addition is followed by addition of MES solution to the leuprolide acetate-microsphere suspension. The suspension is mixed for 15 min. at room temperature, whereupon the suspension is concentrated by diafiltration. To this suspension is added a solution of 17.14 g EDC ((3,3-ethyl-dimethylaminopropyl) carbodiimide) in 25mM MES pH 6.0±0.5 at 0.4 liters per min. The suspension is incubated at room temperature while stirring for 180 min., following which it is diafiltered against 10 vol. Of distilled water and concentrated by diafiltration. The leuprolide acetate content of the suspension is determined whereupon a 50% (w/v) solution of sucrose in water is added and diluted such that the final suspension is approximately 3.75–4.025 mg/mL leuprolide acetate in 5% (w/v) sucrose. This bulk suspension is then filled at 2.0 mL per vial and lyophilized.

(1) Physical Characteristics

Loading characteristics—The $Mg^{2+}$- and $Ca^{2+}$-containing microspheres bound the drug in high yield (>90%), while the $Zn^{2+}$-containing microspheres bound the drug at less than 70% yield.

(2) In Vitro Release

The $Mg^{2+}$- and $Ca^{2+}$-containing microspheres had similar release rates of leuprolide that did not vary with the concentration of metal cation present during microsphere fabrication. At 25 mM Zn2+, the release rate was similar to that of the $Ca^{2+}$and Mg2+-containing microspheres, but at 100 mM Zn2+, the magnitude of the initial "burst" phase was greater.

(3) In Vivo Performance

In rats, at identical dosage of drug, the $Ca^{2+}$- and $Mg^{2+}$-containing microspheres suppressed serum testosterone to castrate levels for at least 4 weeks. The Zn2+-containing microspheres did not suppress testosterone for even three weeks in the rat model.

It should be understood that the preceding is merely a detailed description of certain preferred embodiments. It therefore should be apparent to those skilled in the art that various modifications and equivalents can be made without departing from the spirit and scope of the invention. It is intended to encompass all such modifications within the scope of the appended claims.

All references, patents and patent publications that are recited in this application are incorporated in their entirety herein by reference.

What is claimed is:

1. A method for forming a microsphere comprising:
   (1) forming an aqueous mixture containing:
      (a) a carrier protein;
      (b) a water soluble polymer;
      (c) a polyanionic polysaccharide first complexing agent; and
      (d) a divalent metal cation second completing agent selected from the group consisting of calcium and magnesium;
   (2) allowing the microspheres to form in the aqueous mixture; and
   (3) stabilizing the microspheres, by contacting the microspheres with a crosslinking agent, under conditions sufficient to stabilize the microspheres.

2. The method of claim 1, wherein forming the aqueous mixture is performed by combining the carrier protein, the water soluble polymer, the first-complexing agent, and the second complexing agent essentially simultaneously.

3. The method of claim 1, further comprising the step of:
   (4) contacting the microsphere with a solution of an active agent, to incorporate the active agent into the microsphere.

4. The method of claim 3, wherein the step of contacting the microsphere with the solution of active agent results in a yield of incorporation of at least 60%, of the active agent.

5. The method of claim 3, wherein the active agent is selected from the group consisting of: a hormone, an antibiotic, an antiinfective agent, a hematopoietic, a thrombopoictic agent, an antidementia agent, an antiviral agent, an antitumoral agent, an antipyretic, an analgesic, an antiflammatory agent, an antiulcer agent, an antiallergic agent, an antidepressant, a psychotropic agent, a cardiotonic, an antiaarythmic agent a vasodilator, an antihypcrtensive agent, an antidiabetic agent, an anticoagulant, a cholesterol lowering agent, a therapeutic agent for osteoporosis, an enzyme, a vaccine, an immunological agent, an adjuvant, a cytokine, a growth factor, a nucleotide, a nucleic acid; a carbohydrate, a polysaccharide; a virus, and a virus particle.

6. The method of claim 3, wherein the active agent is a luteinizing hormone releasing hormone or analog thereof.

7. The method of claim 3, wherein the active agent is leuprolide.

8. The method of claim 3, wherein the step of contacting the microsphere with the solution of active agent results in a yield of incorporation of at least 70% of the active agent.

9. The method of claim 3, wherein the step of contacting the microsphere with the solution of active agent results in a yield of incorporation of at least 80% of the active agent.

10. The method of claim 3, wherein the step of contacting the microaphere with the solution of active agent results in a yield of incorporation of at least 90% of the active agent.

11. The method of claim 3, wherein the step of contacting the microsphere with the solution of active agent results in a yield of incorporation of at least 95% of the active agent.

12. The method of claim 3, wherein the step of contacting the microsphere with the solution of active agent results in a yield of incorporation of at least 98% of the active agent.

13. The method of claim 1, wherein the step of stabilizing further comprises exposing the microspheres to an energy source.

14. The method of claim 1, wherein the step of stablizing further comprises exposing the microspheres to heat.

15. A method for forming a microsphere comprising:
   (1) forming an aqueous mixture containing:
      (a) a carrier protein;
      (b) a water soluble polymer;
      (c) a polyanionic polysaccharide first complexing agent; and
      (d) a divalent metal cation second complexing agent selected from the group consisting of calcium and magnesium;
   (2) allowing the microspheres to form in the aqueous mixture; and
   (3) stabile the microspheres by exposing the microspheres to an energy source, under conditions sufficient to stabilize the microspheres.

16. The method of claim 15, wherein the energy source is heat.

17. The method of claim 15 or claim 16, wherein forming the aqueous mixture is performed by combining the carrier protein, the water soluble polymer, the first-complexing agent, and the second complexing agent essentially simultaneously.

18. The method of claim 15, or claim 16, further comprising the step of:
   (4) contacting the microsphere with a solution of an active agent to incorporate the active agent into the microsphere.

19. The method of claim 18, wherein the active agent is selected from the group consisting of: a hormone, an antibiotic, an antiinfective agent a hematopoietic, a thrombopoietic agent, an antidementia agent, an antiviral agent, an antitumoral agent, an antipyretic, an analgesic, an ammatory agent, an antiulcer agent, an antiallergic agent an antidepressant, a psychotropic agent, a cardiotonic, an antiarrythmic agent, a vasodilator, an antihypertensive agent, an antidiabetic agent, an anticoagulnt, a cholesterol lowering agent, a therapeutic agent for osteoporosis, an enzyme, a vaccine, an immunological agent, an adjuvant, a cytokine, a growth factor, a nucleotide, a nucleic acid; a carbohydrate, a polysaccharide; a virus, and a virus particle.

20. The method of claim 18, wherein the active agent is a luteinizg hormone releasing hormone or analog thereof.

21. The method of claim 18, wherein the active agent is leuprolide.

22. The method of claim 15, further comprising the step of:
   (5) stabilizing the microspheres, by contacting the microspheres with a crosslinking agent under conditions sufficient to stabilize the microsphere.

23. The method of claim 18, wherein the step of contacting the microsphere with the solution of active agent results in a yield of incorporation of at least 60% of the active agent.

24. The method of claim 18, wherein the step of contacting the microsphere with the solution of active agent results in a yield of incorporation of at least 700% of the active agent.

25. The method of claim 18, wherein the stop of contacting the microsphere with the solution of active, agent results in a yield of incorporation of at least 80% of the active agent.

26. The method of claim 18, wherein the step of contacting the microsphere with the solution of active agent results in a yield of incorporation of at least 90% of the active agent.

27. The method of claim 18, wherein the step of contacting the microsphere with the solution of active agent results in a yield of incorporation of at least 95% of the active agent.

28. The method of claim 18, wherein the step of contacting the microsphere with the solution of active agent results in a yield of incorporation of at least 98% of the active agent.

* * * * *

UNITED STATES PATENT AND TRADEMARK OFFICE
CERTIFICATE OF CORRECTION

PATENT NO. : 6,458,387 B1
DATED : October 1, 2002
INVENTOR(S) : Scott et al.

It is certified that error appears in the above-identified patent and that said Letters Patent is hereby corrected as shown below:

Column 43,
Line 7, please delete "thrombopoictic" and insert -- thrombopoietic --.
Line 11, please delete "antiaarythmic" and insert -- antiarrythmic --.
Line 11, please delete "antihypcrtensive" and insert -- antihypertensive --.
Line 28, please delete "microaphere" and insert -- microsphere --.
Line 39, please delete "stablizing" and insert -- stabilizing --.
Line 53, please delete "stabile" and insert -- stablizing --.

Column 44,
Line 15, after "agent" please insert -- , --.
Line 17, please delete "ammatory" and insert -- antiinflammatory --.
Line 21, please delete "anticoagulnt" and insert -- anticoagulant --.
Line 27, please delete "luteinizg" and insert -- luteinizing --.
Line 40, please delete "700%" and insert -- 70% --.
Line 42, please delete "stop" and insert -- step --.

Signed and Sealed this

Second Day of March, 2004

JON W. DUDAS
*Acting Director of the United States Patent and Trademark Office*

UNITED STATES PATENT AND TRADEMARK OFFICE
CERTIFICATE OF CORRECTION

PATENT NO.   : 6,458,387 B1
DATED        : October 1, 2002
INVENTOR(S)  : Scott et al.

It is certified that error appears in the above-identified patent and that said Letters Patent is hereby corrected as shown below:

Column 43,
Line 53, please delete "stabile" and insert -- stabilizing --.

Signed and Sealed this

Twenty-first Day of June, 2005

JON W. DUDAS
*Director of the United States Patent and Trademark Office*